United States Patent
Kido et al.

(10) Patent No.: US 11,779,690 B2
(45) Date of Patent: Oct. 10, 2023

(54) OXYGENATOR ANTITHROMBOTIC COATING AND METHOD OF MANUFACTURE

(71) Applicant: TERUMO KABUSHIKI KAISHA, Tokyo (JP)

(72) Inventors: Takayuki Kido, Kanagawa (JP); Takao Anzai, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/693,630

(22) Filed: Mar. 14, 2022

(65) Prior Publication Data

US 2022/0193316 A1 Jun. 23, 2022

Related U.S. Application Data

(63) Continuation of application No. 16/920,877, filed on Jul. 6, 2020, now Pat. No. 11,305,041, which is a
(Continued)

(30) Foreign Application Priority Data

Jan. 10, 2018 (JP) ................... 2018-001806

(51) Int. Cl.
*A61M 1/16* (2006.01)
*A61M 1/36* (2006.01)
(Continued)

(52) U.S. Cl.
CPC ........ *A61M 1/1625* (2014.02); *A61M 1/1645* (2014.02); *A61M 1/1698* (2013.01);
(Continued)

(58) Field of Classification Search
None
See application file for complete search history.

(56) References Cited

U.S. PATENT DOCUMENTS 6,177,013 B1 * 1/2001 Thomas ............... A61L 33/064
264/41
6,495,101 B1 12/2002 Yokoyama et al.
(Continued)

FOREIGN PATENT DOCUMENTS

JP 2006288866 A 10/2006

OTHER PUBLICATIONS

International Search Report, PCT/JP2019/000545, dated Mar. 19, 2019.
(Continued)

*Primary Examiner* — Krishnan S Menon
(74) *Attorney, Agent, or Firm* — MacMillan, Sobanski & Todd, LLC

(57) ABSTRACT

Hollow fiber membranes in an oxygenator for an extracorporeal blood circulator are coated with an antithrombotic polymeric material. The porous hollow fiber membranes for gas exchange have outer surfaces, inner surfaces forming lumens, opening portions through which the outer surfaces communicate with the inner surfaces in a housing. A blood flow path is outside of the hollow fiber membrane bundle in the housing, between a blood inlet port and a blood outlet port. The coating is obtained by filling the blood flow path with a colloidal solution containing an antithrombotic polymeric compound, and moving the colloid solution between the blood inlet port and the blood outlet port for a time that coats a predetermined amount of antithrombotic polymeric compound on the outer surfaces of the hollow fiber membranes. Other surfaces within the oxygenator contacting the blood flow likewise receive the coating.

12 Claims, 9 Drawing Sheets

Related U.S. Application Data continuation of application No. PCT/JP2019/000545, filed on Jan. 10, 2019.

(51) Int. Cl.
    *B01D 63/04*     (2006.01)
    *B01D 67/00*     (2006.01)
    *B01D 71/40*     (2006.01)

(52) U.S. Cl.
    CPC ........... *A61M 1/3673* (2014.02); *B01D 63/04* (2013.01); *B01D 67/0088* (2013.01); *B01D 71/40* (2013.01); *A61M 2202/0225* (2013.01); *A61M 2207/10* (2013.01); *B01D 2325/02* (2013.01)

(56) References Cited

U.S. PATENT DOCUMENTS

| | | | |
|---|---|---|---|
| 7,056,458 B2 * | 6/2006 | Crost | B01D 63/021 |
| | | | 210/500.24 |
| 2010/0135853 A1 * | 6/2010 | Broga | G01N 25/48 |
| | | | 422/51 |
| 2018/0036459 A1 | 2/2018 | Anzai et al. | |

OTHER PUBLICATIONS

Written Opinion of International Search Authority, PCT/JP2019/000545, dated Apr. 2, 2019.

* cited by examiner

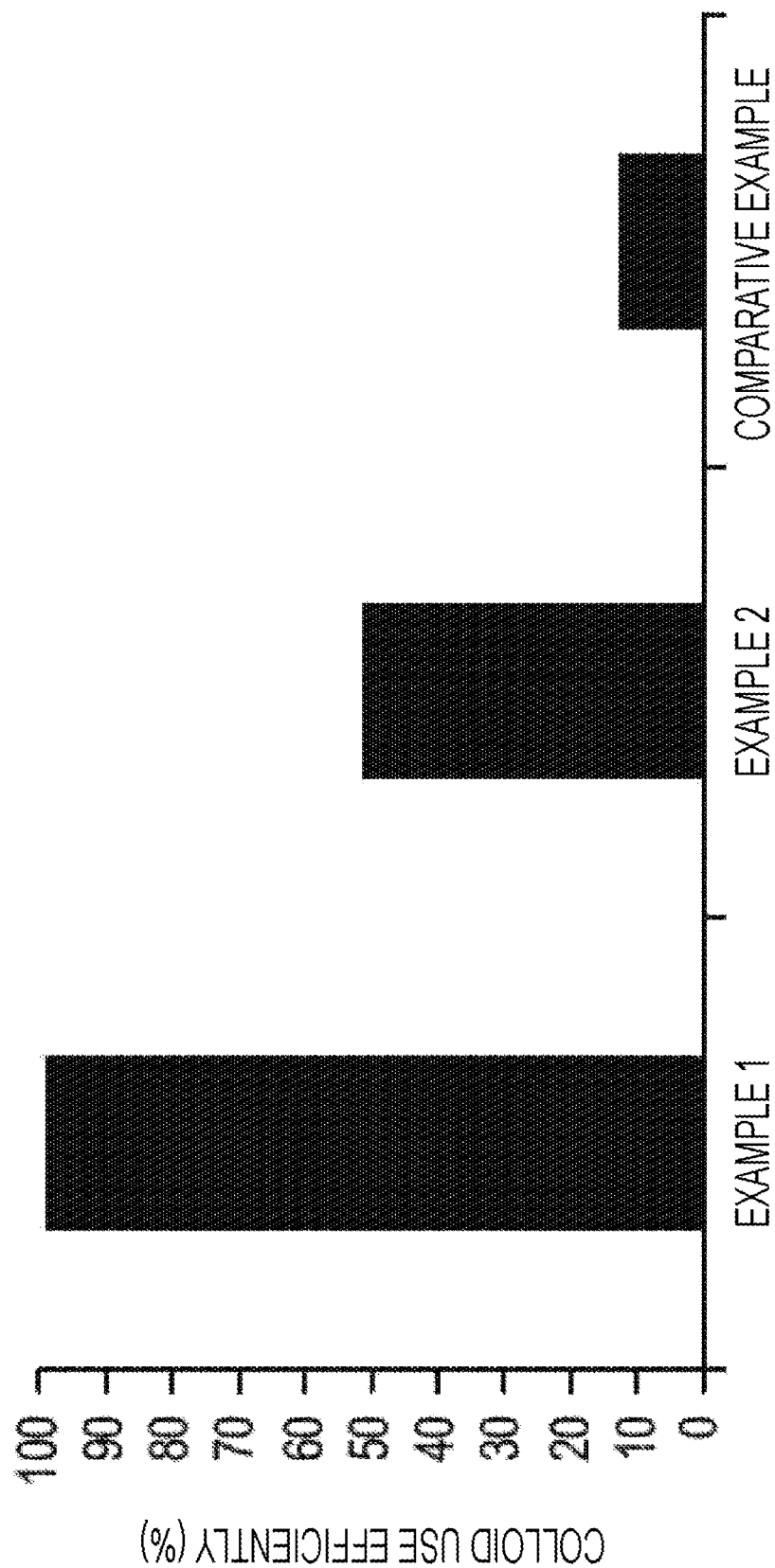

US 11,779,690 B2

OXYGENATOR ANTITHROMBOTIC COATING AND METHOD OF MANUFACTURE

CROSS REFERENCE TO RELATED APPLICATIONS

This application is a continuation of U.S. application Ser. No. 16/920,877, filed Jul. 6. 2020, which is a continuation of PCT Application No. PCT/JP2019/000545, filed Jan. 10, 2019, based on and claiming priority to Japanese Application No. 2018-001806, filed Jan. 10, 2018, all of which are incorporated herein by reference in their entirety.

BACKGROUND OF THE INVENTION

The present invention relates to a method for manufacturing an oxygenator. More specifically, the present invention relates to a method for manufacturing a hollow fiber membrane oxygenator of an outside blood flow type that includes removing carbon dioxide in blood and adding oxygen to blood in extracorporeal blood circulation, and an oxygenator.

Generally, a hollow fiber membrane type oxygenator using porous membranes is widely used as an extracorporeal circulator or an artificial heart-lung apparatus for assisting circulation in open heart surgery for a heart disease. The hollow fiber membranes are used for membrane type oxygenators. Gas exchange in blood is performed through these hollow fiber membranes. As a system of blood flow to the oxygenator, there are an inside flow system in which the blood flows inside of the hollow fiber membranes and gas flows outside of the hollow fiber membranes, and an outside flow system in which, by comparison, the blood flows outside of the hollow fiber membranes and gas flows inside of the hollow fiber membranes.

In hollow fiber membrane type oxygenators, inner surfaces or outer surfaces of the hollow fiber membranes are in contact with the blood. Therefore, there is a concern that the inner surfaces or the outer surfaces of the hollow fiber membranes in contact with the blood may affect adhesion (attachment) or activation of the platelet system. Particularly, an outside flow type oxygenator in which the outer surfaces of the hollow fiber membranes are in contact with the blood causes disruption of a blood flow, which more readily causes adhesion (attachment) or activation of the platelet system.

Considering such problems, and in view of the suppression and prevention effects of alkoxyalkyl(meth)acrylate on adhesion or activation of the platelet system, as an antithrombotic material, alkoxyalkyl(meth)acrylate has been used for coating the blood-contacting surface of hollow fiber membranes of an outside flow type oxygenator. For example, U.S. Pat. No. 6,495,101 B1 discloses a coating method in which outside surfaces or outer surface layers of the hollow fiber membranes are coated with a coating solution obtained by dissolving a polymer containing alkoxyalkyl(meth)acrylate as a main component in a mixed solvent of water, methanol, and ethanol, and then dried.

According to the technique disclosed in U.S. Pat. No. 6,495,101 B1, during the coating process, the coating solution inadvertently penetrates into fine holes (opening portions) from outer surfaces of the hollow fiber membranes, and a part of an inner wall adjacent to the fine holes in the vicinity of the blood flow path side likewise becomes coated with an antithrombotic polymeric compound (antithrombotic polymeric material). When the blood circulates in such an oxygenator, blood plasma components infiltrate into the fine holes along the coating of the antithrombotic polymeric compound formed on the inner wall around the fine holes because of hydrophilicity of the antithrombotic polymeric compound. As a result, this causes leakage of the blood plasma components from the blood flow path side to the gas flow path side.

In order to solve this problem, the inventors of the present invention have prepared a colloidal solution containing an antithrombotic polymeric compound having a predetermined particle size which inhibits migration through the fine holes, and tried to use a method of coating the surfaces of the hollow fiber membranes using the colloidal solution. However, it has been found that this method causes a new problem wherein it is difficult to coat the surfaces of the hollow fiber membranes with a sufficient amount of the antithrombotic polymeric compound.

SUMMARY OF THE INVENTION

Therefore, the present invention has been made in view of the above circumstances, and an object of the present invention is to provide a procedure that can increase a coating amount of the antithrombotic polymeric compound on the hollow fiber membranes in the method for manufacturing an oxygenator using the colloidal solution containing the antithrombotic polymeric compound.

The inventors of the present invention have conducted intensive studies to solve the above problems. As a result, they have found that the above problems can be overcome by filling a blood flow path with a colloidal solution of an antithrombotic polymeric compound, and coating hollow fiber membranes while moving the colloidal solution, and have completed the present invention.

That is, the object can be achieved by a method for manufacturing an oxygenator having a hollow fiber membrane bundle with a plurality of porous hollow fiber membranes for gas exchange which have outer surfaces, inner surfaces forming lumens, opening portions (e.g., fine holes) through which the outer surfaces communicate with the inner surfaces in a housing, a blood flow path which is outside of the hollow fiber membrane bundle in the housing, a blood inlet port in an upper position of the blood flow path, and a blood outlet port in a lower position of the blood flow path, the method including: filling the blood flow path with a colloidal solution containing an antithrombotic polymeric compound; and moving the colloid solution between the blood inlet port and the blood outlet port. Furthermore, the object is achieved by an oxygenator for an extracorporeal blood circulator, comprising: a housing having a blood inlet port, a blood outlet port, and housing surfaces for defining a blood flow path in an inner chamber; a hollow fiber membrane bundle retained in the inner chamber with a plurality of porous hollow fiber membranes for gas exchange which have outer surfaces, inner surfaces forming lumens, and opening portions through which the outer surfaces communicate with the inner surfaces, wherein the blood flow path passes over the outside surfaces of the hollow fiber membranes in the inner chamber; and a coating of an antithrombotic polymeric compound on the outside surfaces of the hollow fiber membranes; wherein the coating is deposited on the outside surfaces of the hollow fiber membranes by filling the blood flow path with a colloidal solution containing an antithrombotic polymeric compound, and moving the colloidal solution along the blood flow path between the blood inlet port and the blood outlet port for a time that coats a predetermined amount of antithrombotic polymeric compound on the outer surfaces of the hollow fiber membranes.

BRIEF DESCRIPTION OF DRAWINGS

FIG. 9 is a graph showing colloid use efficiencies in Examples and Comparative Example.

DETAILED DESCRIPTION OF PREFERRED EMBODIMENTS

Figure 1:
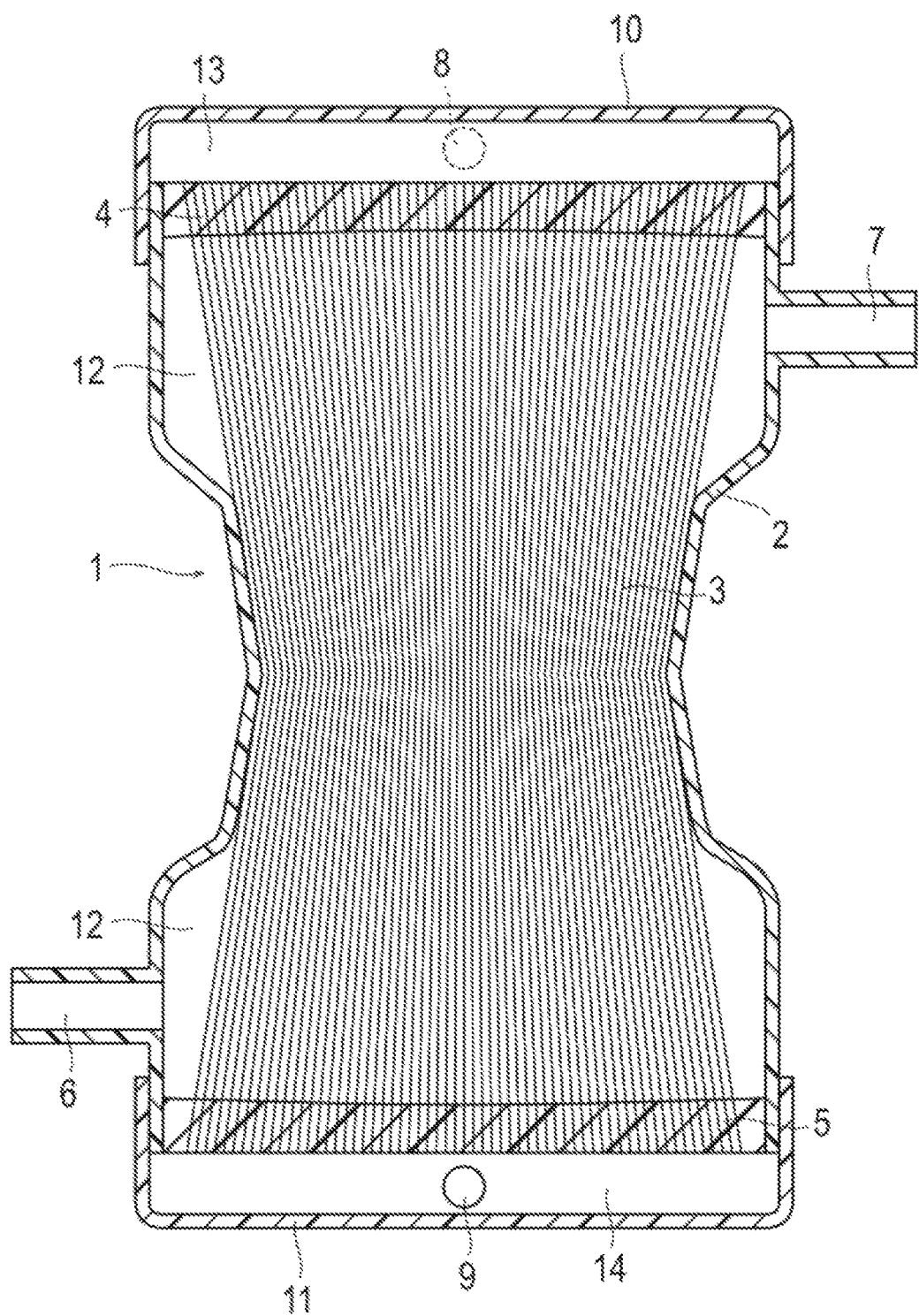
FIG. 1 is a cross-sectional view showing one embodiment of a hollow fiber membrane oxygenator of an outside blood flow type according to the present invention.

The present invention relates to a method for manufacturing an oxygenator having a hollow fiber membrane bundle with a plurality of porous hollow fiber membranes for gas exchange which have outer surfaces, inner surfaces forming lumens, opening portions through which the outer surfaces communicate with the inner surfaces in a housing, a blood flow path which is outside of the hollow fiber membrane bundle in the housing, a blood inlet port in an upper position of the blood flow path, and a blood outlet port in a lower position of the blood flow path, the method including: filling the blood flow path with a colloidal solution containing an antithrombotic polymeric compound; and circulating the colloid solution between the blood inlet port and the blood outlet port. According to the present invention, in the method for manufacturing an oxygenator using the colloidal solution containing the antithrombotic polymeric compound, the coating amount of the antithrombotic polymeric compound on the hollow fiber membranes can be increased.

In the method for manufacturing an oxygenator according to the present invention, in the hollow fiber membrane oxygenator of an outside blood flow type, a blood flow path is filled with the colloidal solution containing the antithrombotic polymeric compound, and the colloidal solution is circulated (e.g., moved) between the blood inlet port and the blood outlet port, whereby the coating amount of the antithrombotic polymeric compound can be increased. The mechanism in which the above effect is exerted through such a process is not clear, but the inventors of the present invention speculate as follows. The present invention is not limited to the following mechanism.

The colloid particles (surfaces of particles) and the surfaces of the hollow fiber membranes in the colloidal solution containing the antithrombotic polymeric compound are typically negatively charged. For this reason, the colloid particles repel other colloid particles present in the surroundings, and also repel the surfaces of the hollow fiber membranes. Accordingly, it has been difficult to coat the surfaces of the hollow fiber membranes with a sufficient amount of the colloid particles (the antithrombotic polymeric compound). In the present invention, the blood flow path is filled with the colloidal solution, and the colloidal solution is moved between the blood inlet port and the blood outlet port, whereby the colloid particles can collide with the surfaces of the hollow fiber membranes. As described above, it is considered that the colloid particles collide with the surfaces of the hollow fiber membranes with energy larger than the electric repulsive force, so that the colloid particles are easily fixed to the surfaces of the hollow fiber membranes, and the coating amount of the antithrombotic polymeric compound is increased.

In addition, the colloidal solution is circulated, whereby the number of times that colloid particles come into contact with the surfaces of the hollow fiber membranes can be increased as compared with a case where the colloidal solution is allowed to stand. For this reason, even in a case where a colloidal solution having a low colloid concentration is used, it is possible to coat the surfaces of the hollow fiber membranes with a sufficient amount of the antithrombotic polymeric compound (i.e., it is possible to improve the colloid use efficiency in the colloidal solution).

Hereinafter, preferred embodiments of the present invention will be described. Note that the present invention is not limited to only the following embodiments. In addition, dimensional ratios in the drawings are exaggerated for convenience of description, and may be different from actual dimensional ratios.

In the present specification, "X to Y" indicating a range includes X and Y, and means "X or more and Y or less". Unless otherwise specified, operation and measurements of physical properties or the like are performed under conditions of room temperature (20° C. to 25° C.) and a relative humidity of 40 to 50% RH.

One aspect of the present invention is a method for manufacturing an oxygenator having a hollow fiber membrane bundle with a plurality of porous hollow fiber membranes for gas exchange which have outer surfaces, inner surfaces forming lumens, opening portions through which the outer surfaces communicate with the inner surfaces in a housing, a blood flow path which is outside of the hollow fiber membrane bundle in the housing, a blood inlet port in an upper position of the blood flow path, and a blood outlet port in a lower position of the blood flow path, the method including: filling the blood flow path with a colloidal solution containing an antithrombotic polymeric compound; and moving the colloid solution between the blood inlet port and the blood outlet port.

Hereinafter, the method for manufacturing an oxygenator of the present invention will be described in detail. In the present specification, for convenience, an oxygenator obtained by the manufacturing method of the present invention will be first described, and then the manufacturing method of the present invention will be described.

Figure 2:
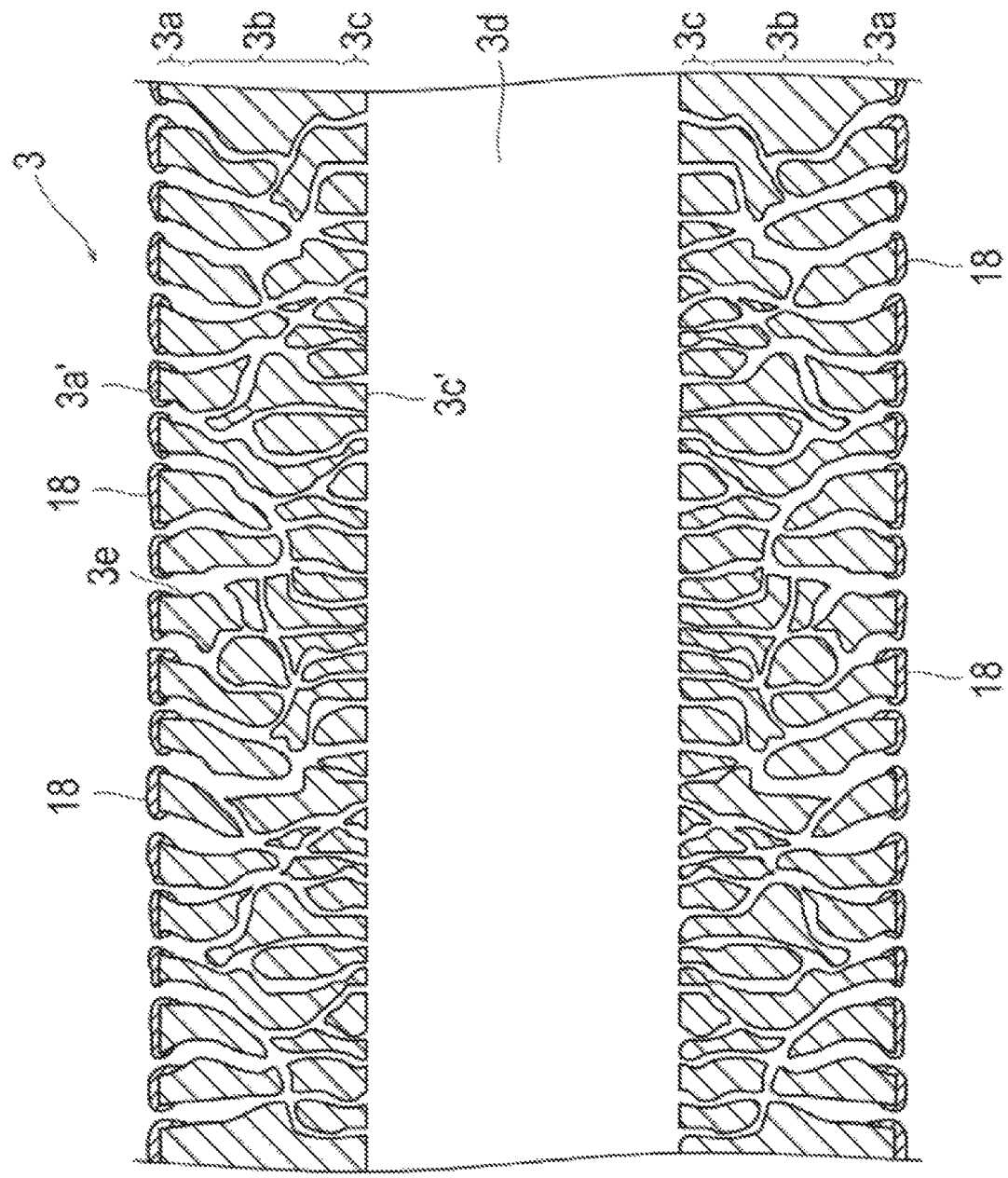
FIG. 2 is an enlarged cross-sectional view of a hollow fiber membrane used in the hollow fiber membrane oxygenator of an outside blood flow type according to the present invention.
Figure 3:
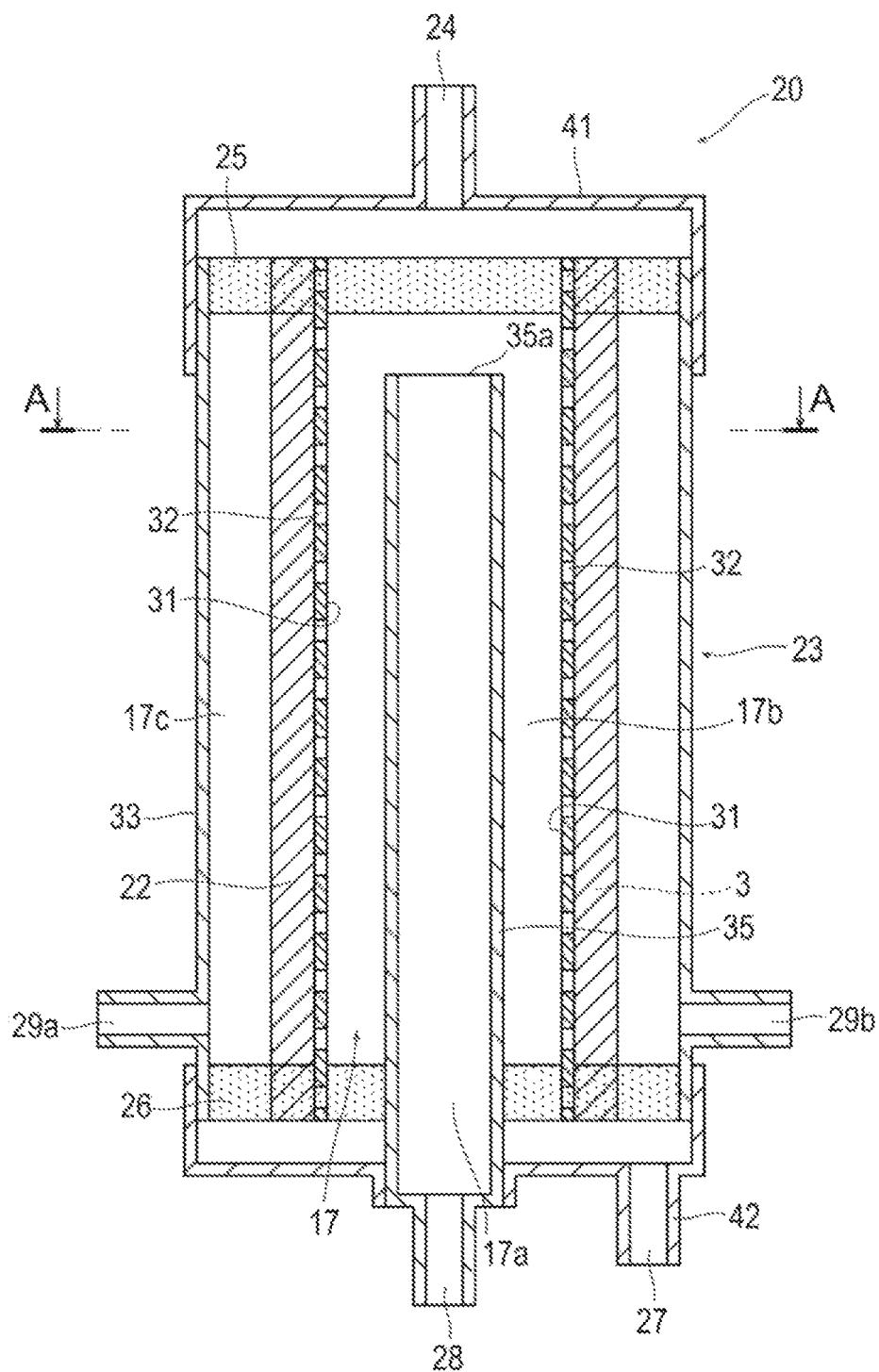
FIG. 3 is a cross-sectional view showing another embodiment of a hollow fiber membrane oxygenator of an outside blood flow type according to the present invention.

FIG. 1 is a cross-sectional view of one embodiment of a hollow fiber membrane oxygenator of an outside blood flow type according to the present invention. FIG. 2 is an enlarged cross-sectional view of porous hollow fiber membranes for gas exchange used in the hollow fiber membrane oxygenator of an outside blood flow type according to the present invention. FIG. 3 is a cross-sectional view of another embodiment of an oxygenator according to the present invention.

In FIG. 1, an oxygenator 1 is an oxygenator of a type in which a large number of porous hollow fiber membranes 3 for gas exchange are accommodated in a housing 2. The blood flows around and over the outer side of the hollow fiber membranes 3, and an oxygen-containing gas flows through the inside of the hollow fiber membranes 3. In FIG. 2, an antithrombotic polymeric compound 18 coats the outside surface of the hollow fiber membrane 3 which serves as the blood contact portion (an outer surface 3a', or an outer surface 3a', and an outer surface layer 3a). The coat (coating) of the antithrombotic polymeric compound 18 is selectively formed on the outer surface 3a' of the hollow fiber membrane 3. FIG. 2 shows an aspect where the coat (coating) of the antithrombotic polymeric compound 18 is formed on the outer surface 3a' of the hollow fiber membrane used in the hollow fiber membrane oxygenator of an outside blood flow type. In the hollow fiber membrane of such an aspect, the outer surface 3a' side is in contact with the blood, and the oxygen-containing gas flows into an inner surface 3c' side.

Note that "the antithrombotic polymeric compound coats the outside surface of the hollow fiber membrane" means that the coat (coating) of the antithrombotic polymeric compound is formed on the outer surface of the hollow fiber membrane (a surface on the side where the blood flows) or on the outer surface and the outer surface layer. On the other hand, "the antithrombotic polymeric compound coats the outer surface of the hollow fiber membrane" means that the coat (coating) of the antithrombotic polymeric compound is formed on the outer surface of the hollow fiber membrane (a surface on the side where the blood flows). Further, "the antithrombotic polymeric compound coats the outer surface layer of the hollow fiber membrane" means that the antithrombotic polymeric compound penetrates into a part of the outer surface layer of the hollow fiber membrane (in the vicinity of the outer surface of the fine holes) to form the coat (coating). The coat (coating) of the antithrombotic polymeric compound may be formed on at least a part of the blood contact portion (outer surface) of the hollow fiber membrane. From the viewpoint of the antithrombotic activity and biocompatibility (the suppression and prevention effects of adhesion and attachment of the platelets and the suppression and prevention effects of activation of the platelets), it is preferable that the coating be formed on the entire blood contact portion of the hollow fiber membrane (outer surface). That is, the antithrombotic polymeric compound preferably coats the entire blood contact portion of the oxygenator (outer surface).

In the embodiment according to FIG. 2, the antithrombotic polymeric compound may exist on an internal layer 3b or an inner surface layer 3c of the hollow fiber membrane 3, but it is preferable that no substantial material exist on the internal layer 3b or the inner surface layer 3c of the hollow fiber membrane 3. In the present specification, "no substantial antithrombotic polymeric compound exists on the internal layer 3b or the inner surface layer 3c of the hollow fiber membrane 3" means that the penetration of the antithrombotic polymeric compound is not observed in the vicinity of the inside surface of the hollow fiber membrane (a surface on the side where the oxygen-containing gas flows). In the method for manufacturing an oxygenator according to the present invention, the coating is formed by applying the colloidal solution of the antithrombotic polymer. Therefore, it is possible to achieve an aspect in which no substantial antithrombotic polymeric compound exists on the internal layer 3b or the inner surface layer 3c of the hollow fiber membrane 3.

A hollow fiber membrane type oxygenator 1 according to the present embodiment includes: a housing 2 having a blood inlet port 6 and a blood outlet port 7; a hollow fiber membrane bundle having a large number of porous hollow fiber membranes 3 for gas exchange accommodated in the housing 2; a pair of partition walls 4 and 5 liquid-tightly supporting both end portions of the hollow fiber membrane bundle within the housing 2; a blood chamber 12 formed between the inside surface of the housing 2 and the partition walls 4 and 5, and the outside surfaces of the hollow fiber membranes 3; a gas chamber formed inside the hollow fiber membranes 3; and a gas inlet port 8 and a gas outlet port 9 communicating with the gas chamber.

Specifically, the hollow fiber membrane type oxygenator 1 of the present embodiment includes the tubular housing 2, an aggregate of the hollow fiber membranes 3 for gas exchange accommodated in the tubular housing 2, and the partition walls 4 and 5 liquid-tightly retaining both end portions of the hollow fiber membranes 3 within the housing 2. The tubular housing 2 is partitioned into the blood chamber 12 that is a first fluid chamber and the gas chamber that is a second fluid chamber. The blood inlet port 6 and the blood outlet port 7 communicating with the blood chamber 12 are provided in the tubular housing 2.

A cap-like gas inlet side header 10 having the gas inlet port 8 that is a second fluid inlet port communicating with the gas chamber that is the inner spaces of the hollow fiber membranes 3, is attached above the partition walls 4 that are the end portion of the tubular housing 2. A gas inlet chamber 13 is formed of the outside surface of the partition walls 4 and the inside surface of the gas inlet side header 10. The gas inlet chamber 13 communicates with the gas chamber that is formed of the inner spaces of the hollow fiber membranes 3.

Similarly, a cap-like gas outlet side header 11 having a gas outlet port 9 that is a second fluid outlet port communicating with the inner spaces of the hollow fiber membranes 3, is attached below the partition walls 5. Therefore, a gas outlet chamber 14 is formed of the outside surface of the partition walls 5 and the inside surface of the gas outlet side header 11.

The hollow fiber membranes 3 are porous membranes made of a hydrophobic polymer material. Membranes similar to hollow fiber membranes for use in a known oxygenator are used and are not particularly limited. The hollow fiber membranes (particularly, the inside surfaces of the hollow fiber membranes) are made of a hydrophobic polymer material, and thus the leakage of blood plasma components can be suppressed.

Here, an inner diameter of the hollow fiber membrane is not particularly limited and is preferably 50 to 300 µm, more preferably 100 to 250 µm, and still more preferably 150 to 200 µm. An outer diameter of the hollow fiber membrane is not particularly limited and is preferably 100 to 400 µm, more preferably 200 to 350 µm, and still more preferably 250 to 300 µm. A wall thickness (membrane thickness) of the hollow fiber membrane is preferably 20 µm to 100 µm, more preferably 25 to 80 µm, still more preferably 25 to 70 µm, and particularly preferably 25 to 60 µm. In the present specification, "the wall thickness (membrane thickness) of the hollow fiber membrane" means a wall thickness between the inner surface and the outer surface of the hollow fiber membrane, and is calculated by using the expression: [(outer diameter of hollow fiber membrane)−(inner diameter of hollow fiber membrane)]/2. Here, a lower limit of the wall thickness of the hollow fiber membrane is set as above, so that it is possible to secure the sufficient strength of the hollow fiber membranes. Further, it is satisfactory in terms of labor and cost in manufacturing, and is also preferable from the viewpoint of mass production. Furthermore, porosity of the hollow fiber membrane is preferably 5 to 90% by volume, more preferably 10 to 80% by volume, and particularly preferably 30 to 60% by volume. A fine hole size of the hollow fiber membrane (i.e., a hole size of the opening portion of the hollow fiber) is not particularly limited and is preferably 10 nm to 5 µm, more preferably 50 nm to 1 µm, and particularly preferably 50 nm to 100 nm.

In the present specification, a diameter of an opening portion of a hollow fiber membrane" indicates an average diameter of the opening portion on a side (the outer surface side in the present embodiment) that is coated with the antithrombotic polymeric compound (may simply be referred to as "fine hole" in the present specification). Further, an average diameter of the opening portion (may simply be referred to as "hole size" or "fine hole size" in the present specification) is measured by a method described below.

First, an SEM image of a side (the outer surface in the present embodiment) of the hollow fiber membranes to be coated with the antithrombotic polymeric compound is captured using a scanning electron microscope (SEM). Next, the obtained SEM image is subjected to an image process, the hole portion (opening portion) is set to white, the other portions are inverted to black, and the number of pixels in the white portion is measured. A boundary level of binarization is an intermediate value of a difference between the whitest portion and the blackest portion.

Subsequently, the number of pixels of the hole displaying white (opening portion) is measured. A hole area is calculated based on the number of pixels of the hole and a resolution (pm/pixel) of the SEM image obtained as described above. From the obtained hole area, a diameter of each hole is calculated assuming the hole to be circular. A diameter of, for example, 500 holes is extracted, which is a statistically significant and random number, and an arithmetic average thereof is set as an average diameter of the opening portion of the hollow fiber.

As a material used for the porous membranes, a material similar to a material used as the hollow fiber membranes in a known oxygenator can be used. Specific examples thereof include polyolefin resins such as polypropylene and polyethylene, and hydrophobic polymer materials such as polysulfone, polyacrylonitrile, polytetrafluoroethylene, and cellulose acetate. Among these, a polyolefin resin is preferably used, and polypropylene is more preferable. The method for manufacturing hollow fiber membranes is not particularly limited, and a known method for producing hollow fiber membranes can be applied similarly or appropriately modified and applied. For example, it is preferable that micro fine holes be formed on the walls of the hollow fiber membranes through a stretching method or a solid-liquid phase separation method.

As a material constituting the tubular housing 2, a material similar to a material used for a housing of a known oxygenator can be used. Specific examples thereof include hydrophobic synthetic resins such as polycarbonate, acrylic-styrene copolymer, and acrylic-butylene-styrene copolymer. A shape of the housing 2 is not particularly limited, and is preferably cylindrical and transparent, for example. The inside thereof can be easily confirmed by forming the housing to be transparent.

An accommodation amount of the hollow fiber membranes in the present embodiment is not particularly limited, and an amount similarly to an amount for use in a known oxygenator can be applied. For example, about 5,000 to 100,000 porous hollow fiber membranes 3 are accommodated in parallel in the housing 2 in an axial direction thereof. Further, both the ends of the hollow fiber membranes 3 are respectively open towards both the ends of the housing 2, and the hollow fiber membranes 3 are fixed in a liquid-tight state by the partition walls 4 and 5. The partition walls 4 and 5 are formed by a potting agent such as polyurethane or silicone rubber. A portion interposed between the partition walls 4 and 5 in the housing 2 is divided into the gas chamber inside the hollow fiber membranes 3 and the blood chamber 12 outside the hollow fiber membranes 3.

In the present embodiment, the gas inlet side header 10 having the gas inlet port 8 and the gas outlet side header 11 having the gas outlet port 9 are liquid-tightly attached to the housing 2. These headers may be formed of any material, and can be formed of a hydrophobic synthetic resin used for the housing described above, for example. The header may be attached by any method. For example, the header can be attached to the housing 2 by fusion bonding using ultrasound waves, high frequency waves, induction heating, and the like, by adhesion with an adhesive, or by mechanical engagement. In addition, the attachment may be performed by using a fastening ring (not shown). It is preferable that the entire blood contact portion of the hollow fiber membrane type oxygenator 1 (the inside surface of the housing 2, the outside surfaces of the hollow fiber membranes 3) be formed of a hydrophobic material.

As shown in FIG. 2, the antithrombotic polymeric compound 18 coats at least the outer surface $3a'$ (and optionally, the outer surface layer $3a$; hereinafter the same applies) of the hollow fiber membrane 3 which serves as the blood contact portion of the hollow fiber membrane type oxygenator 1. As described above, it is preferable that no substantial antithrombotic polymeric compound exist on the internal layer $3b$ or the inner surface layer $3c$ of the hollow fiber membrane. In the case no substantial antithrombotic polymeric compound exists, hydrophobic properties of the base material itself of the membrane are maintained as they are on the internal layer $3b$ or the inner surface layer $3c$ of the hollow fiber membrane, and therefore the leakage of blood plasma components can be effectively prevented. Particularly, it is preferable that no substantial antithrombotic polymeric compound exist on both the internal layer $3b$ and the inner surface layer $3c$ of the hollow fiber membrane. Further, the hollow fiber membrane 3 includes, in the center, a passage (lumen) $3d$ forming the gas chamber. In addition, the hollow fiber membrane 3 includes an opening portion $3e$ through which the outer surface $3a'$ and the inner surface $3c'$ thereof communicate with each other. In the hollow fiber membrane having such a configuration, the blood comes into contact with the outer surface $3a'$ coated with the antithrombotic polymeric compound 18. Meanwhile, the oxygen-containing gas flows and contacts the inner surface $3c'$.

In the present embodiment, the coat (coating) of the antithrombotic polymeric compound is selectively formed on the outer surfaces of the hollow fiber membranes (outside flow type). For this reason, the blood (particularly, blood plasma components) is unlikely to or does not penetrate into the inside of the fine holes of the hollow fiber membranes. Therefore, it is possible to effectively suppress or prevent blood (particularly, blood plasma components) leakage from the hollow fiber membranes. Particularly, in a case where no substantial antithrombotic polymeric compound exists on the internal layers 3b of the hollow fiber membranes and the inner surface layers 3c of the hollow fiber membranes, the hydrophobic state of the material is maintained on the internal layers 3b of the hollow fiber membranes and the inner surface layers 3c of the hollow fiber membranes, and therefore leakage of a large amount of blood (particularly, blood plasma components) can be further effectively suppressed or prevented. Accordingly, in an oxygenator obtained by the method of the present invention, a high level of gas exchange capacity can be maintained for a long period of time.

It is essential that the antithrombotic polymeric compound coating according to the present embodiment be formed on the outer surfaces of the hollow fiber membranes of the oxygenator. The coating may be formed on another constituent member (for example, on the entire blood contact portion) in addition to the outer surfaces. In the case of having the configuration, adhesion, attachment, and activation of the platelets can be further effectively suppressed or prevented in the entire blood contact portion of the oxygenator. In addition, since a contact angle of the blood contact surface decreases, this can facilitate a priming operation. In this case, it is preferable that the antithrombotic polymeric compound coating according to the present invention be formed on the other constituent member in contact with the blood. The antithrombotic polymeric compound does not coat a portion other than the blood contact portions of the hollow fiber membranes, or on another portion of the hollow fiber membranes (for example, a portion buried in the partition walls). Such a portion is not in contact with the blood, and therefore, the antithrombotic polymeric compound not being coated thereon does not cause a particular problem.

In addition, the oxygenator obtained by the method of the present invention may be a type shown in FIG. 3. FIG. 3 is a cross-sectional view showing another embodiment of an oxygenator obtained by the method of the present invention. Furthermore, FIG. 4 is a cross-sectional view taken along line A-A of FIG. 3.

In FIG. 3, an oxygenator (hollow fiber membrane oxygenator of an outside blood flow type) 20 includes an inner tubular member 31 having a blood circulation opening 32 on a side surface thereof, a tubular hollow fiber membrane bundle 22 having the large number of porous hollow fiber membranes 3 for gas exchange and wound around an outside surface of the inner tubular member 31, a housing 23 accommodating the tubular hollow fiber membrane bundle 22 together with the inner tubular member 31, partition walls 25 and 26 fixing both end portions of the tubular hollow fiber membrane bundle 22 within the housing in a state where both the ends of the hollow fiber membranes 3 are open, a blood inlet port 28 and blood outlet ports 29a and 29b communicating with a blood chamber 17 formed in the housing 23, and a gas inlet port 24 and a gas outlet port 27 communicating with the insides of the hollow fiber membranes 3.

Figure 4:
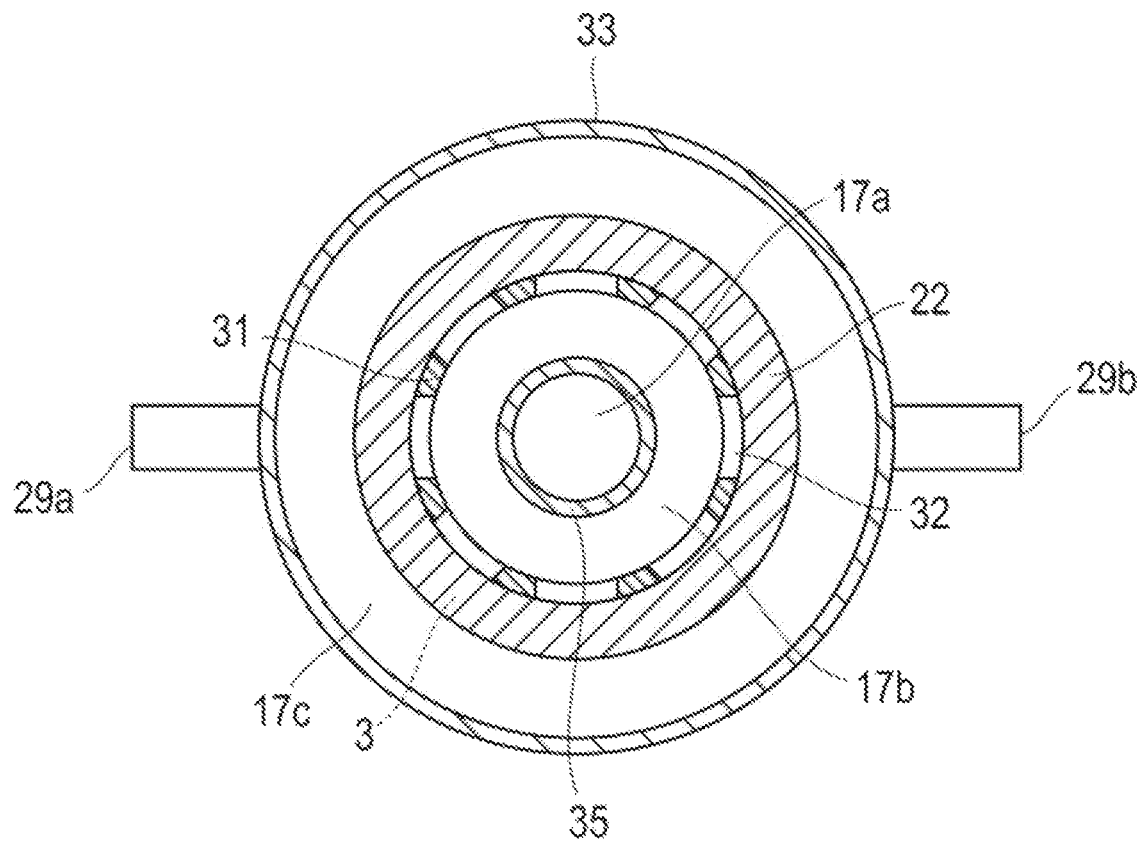
FIG. 4 is a cross-sectional view taken along line A-A of FIG. 3.

In the oxygenator 20 of the present embodiment, as shown in FIG. 3 and FIG. 4, the housing 23 has an outer tubular member 33 accommodating the inner tubular member 31, and the tubular hollow fiber membrane bundle 22 is accommodated between the inner tubular member 31 and the outer tubular member 33. Further, the housing 23 has one of the blood inlet port or the blood outlet port communicating with the inside of the inner tubular member, and the other one of the blood inlet port or the blood outlet port communicating with the inside of the outer tubular member.

Specifically, in the oxygenator 20 of the present embodiment, the housing 23 has an inner tubular body 35 that is accommodated in the outer tubular member 33 and the inner tubular member 31, and in which a distal end thereof is open in the inner tubular member 31. The blood inlet port 28 is formed on one end (lower end) of the inner tubular body 35, and the two blood outlet ports 29a and 29b extending outwards are formed on a side surface of the outer tubular member 33. There may be one or a plurality of the blood outlet ports.

The tubular hollow fiber membrane bundle 22 is wound around the outside surface of the inner tubular member 31. That is, the inner tubular member 31 is a core of the tubular hollow fiber membrane bundle 22. A distal end portion of the inner tubular body 35 accommodated inside the inner tubular member 31 is open in the vicinity of the first partition walls 25. In addition, the blood inlet port 28 is formed on a protruding lower end portion by the inner tubular member 31.

Each of the inner tubular body 35, the inner tubular member 31 where the hollow fiber membrane bundle 22 is wound around the outside surface thereof, and the outer tubular member 33 is arranged almost concentrically. One end (upper end) of the inner tubular member 31 where the hollow fiber membrane bundle 22 is wound around the outside surface thereof, and one end (upper end) of the outer tubular member 33 maintain the concentric positional relationship between each other by the first partition walls 25, and are in the liquid-tight state where a space formed between the inside of the inner tubular member 31 and the inner tubular body 35, and a space formed between the outside surfaces of the hollow fiber membrane bundle 22 and the outer tubular member 33 do not communicate with the outside.

Further, a portion that is in a slightly upper position than the blood inlet port 28 of the inner tubular body 35, the other end (lower end) of the inner tubular member 31 where the hollow fiber membrane bundle 22 is wound around the outside surface thereof, and the other end (lower end) of the outer tubular member 33 maintain the concentric positional relationship between each other by the second partition walls 26. The above components are in a liquid-tight state where a space formed between the inside of the inner tubular member 31 and the inner tubular body 35, and a space formed between the outside surfaces of the hollow fiber membrane bundle 22 and the outer tubular member 33 do not communicate with the outside. Furthermore, the partition walls 25 and 26 are formed by a potting agent such as polyurethane or silicone rubber.

Therefore, the oxygenator 20 of the present embodiment includes a blood inlet portion 17a formed by the inside of the inner tubular body 35, a first blood chamber 17b that is a substantially tubular space formed between the inner tubular body 35 and the inner tubular member 31, and a second blood chamber 17c that is a substantially tubular space formed between the hollow fiber membrane bundle 22 and the outer tubular member 33, and thereby the blood chamber 17 is formed.

The blood flowing from the blood inlet port 28 flows into the blood inlet portion 17a, moves up in the inner tubular body 35 (blood inlet portion 17a), flows out from an upper end 35a (opening end) of the inner tubular body 35, flows into the first blood chamber 17b, passes through an opening 32 formed in the inner tubular member 31, comes into contact with the hollow fiber membranes, and after gas exchange, flows into the second blood chamber 17c, and flows out from the blood outlet ports 29a and 29b.

Further, a gas inlet member 41 having the gas inlet port 24 is fixed to one end of the outer tubular member 33, and similarly, a gas outlet member 42 having the gas outlet port 27 is fixed to the other end of the outer tubular member 33. The blood inlet port 28 of the inner tubular body 35 protrudes through the gas outlet member 42.

The outer tubular member 33 is not particularly limited, and a member having a tubular body, a polygonal tube, an elliptical shape in the cross section, and the like can be used. The member is preferably the tubular body. Further, an inner diameter of the outer tubular member is not particularly limited, and the inner diameter of the outer tubular member can be a diameter similar to a diameter for use in a known oxygenator. It is suitable that the diameter be approximately 32 to 164 mm. Furthermore, an effective length of the outer tubular member (the portion of the length of the outer tubular member that is not buried in the partition walls) is not particularly limited, and the length can be an effective length similar to the effective length of the outer tubular member for use in a known oxygenator. It is suitable that the effective length of the outer tubular member be approximately 10 to 730 mm.

Furthermore, a shape of the inner tubular member 31 is not particularly limited, and for example, a member having a tubular body, a polygonal tube, an elliptical shape in the cross section, and the like can be used. The member is preferably the tubular body. Furthermore, an outer diameter of the inner tubular member is not particularly limited, and the outer diameter can be an outer diameter similar to the outer diameter of the inner tubular member for use in a known oxygenator. It is suitable that the outer diameter be approximately 20 to 100 mm. Furthermore, the effective length of the inner tubular member (the portion of the length of the inner tubular member that is not buried in the partition walls) is not particularly limited, and the length can be an effective length similar to the effective length of the inner tubular member for use in a known oxygenator. It is suitable that the effective length of the inner tubular member be approximately 10 to 730 mm.

Figure 5:
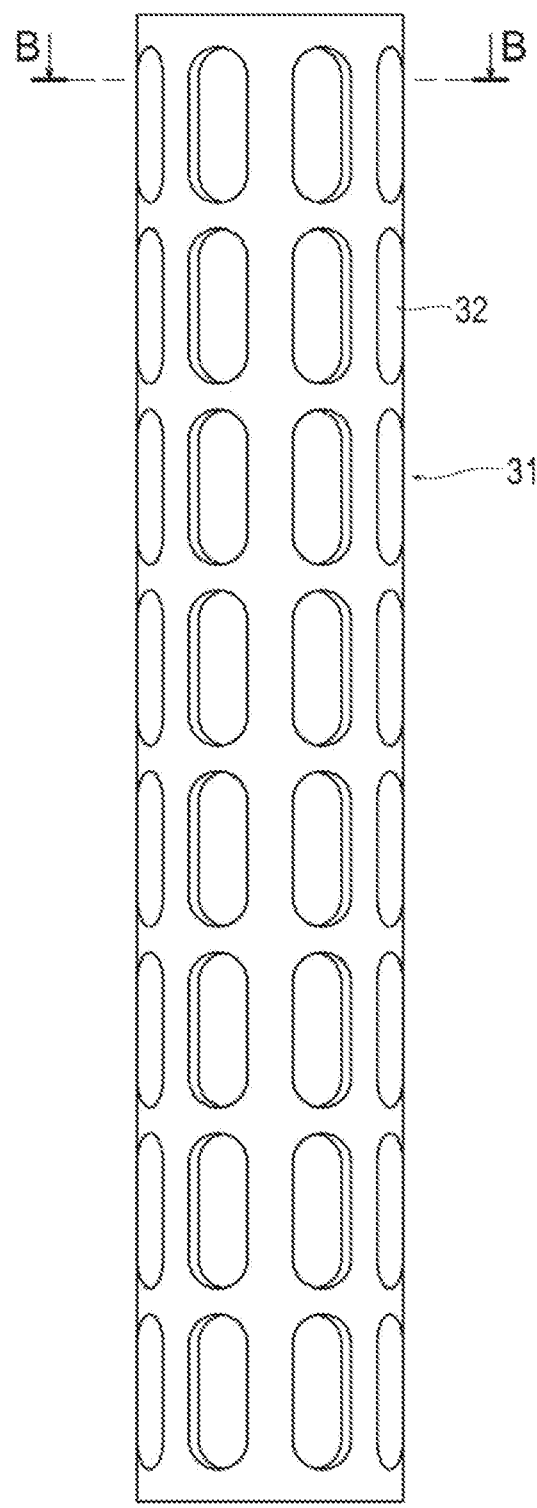
FIG. 5 is a front view showing an example of an inner tubular member used in the hollow fiber membrane oxygenator of an outside blood flow type according to the present invention.
Figure 6:
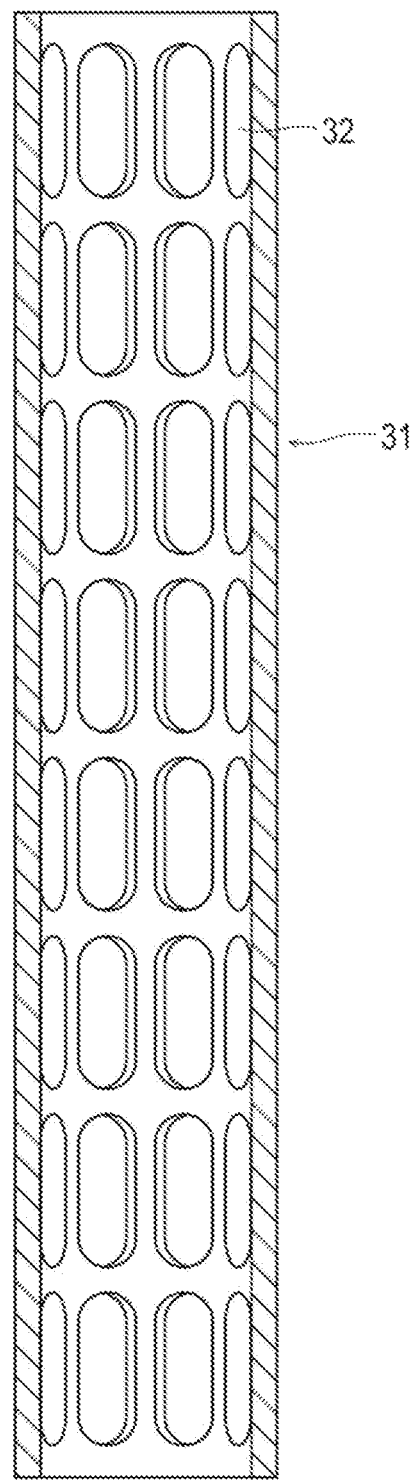
FIG. 6 is a central longitudinal cross-sectional view of the inner tubular member shown in FIG. 5.
Figure 7:
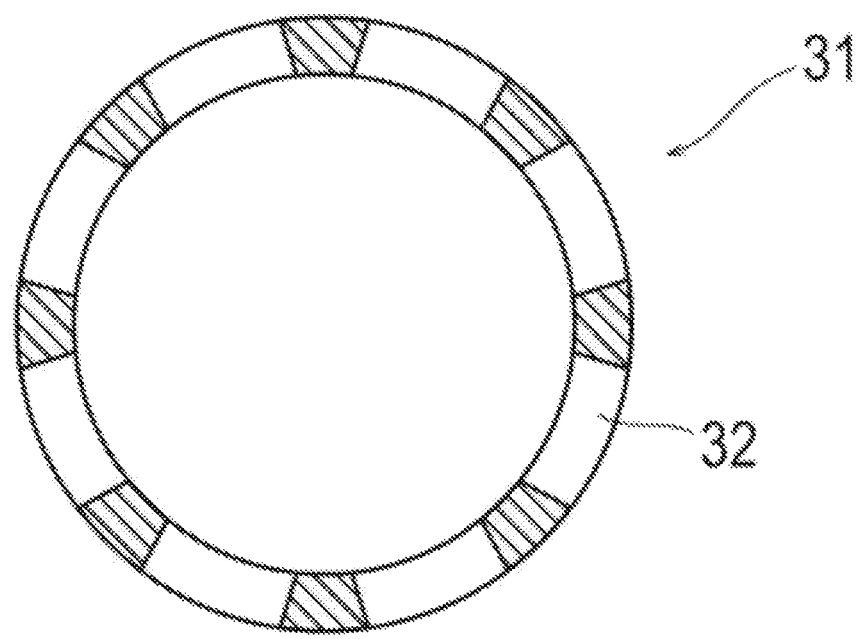
FIG. 7 is a cross-sectional view taken along line B-B of FIG. 5.

The inner tubular member 31 includes a large number of blood circulation openings 32 on the side surface thereof. Regarding a size of the opening 32, it is preferable that a total area be large as long as the required strength of the tubular member is maintained. As shown in FIG. 5 that is a front view, FIG. 6 that is a central longitudinal cross-sectional view of FIG. 5, and FIG. 7 that is a cross-sectional view taken along line B-B of FIG. 5, as a tubular member satisfying such conditions, for example, it is suitable to use a tubular member having a plurality of sets (8 sets for periphery, in the drawings) of circularly arranged openings in which a plurality of the openings 32 is provided on an outer peripheral surface of the tubular member at an equal angle and interval (for example, each set includes 4 to 24 openings, in the drawings, 8 openings are arranged in a longitudinal direction) and which is provided in an axial direction of the tubular member at an equal interval. Further, an opening shape may be a circle, a polygon, an ellipse, and the like, but an oval shape is suitable as shown in FIG. 5.

In addition, a shape of the inner tubular body 35 is not particularly limited, and for example, a body having a tubular body, a polygonal tube, an elliptical shape in the cross section, and the like can be used. The member is preferably the tubular body. Further, a distance between a distal end opening of the inner tubular body 35 and the first partition walls 25 is not particularly limited, and a distance similar to a distance for use in a known oxygenator can be applied. It is suitable that the distance be approximately 20 to 50 mm. Furthermore, an inner diameter of the inner tubular body 35 is not particularly limited, and the inner diameter can be an inner diameter similar to an inner diameter of the inner tubular body for use in a known oxygenator. It is suitable that the inner diameter of the inner tubular body be approximately 10 to 30 mm.

A thickness of the tubular hollow fiber membrane bundle 22 is not particularly limited, and the thickness can be a thickness similar to a thickness of the tubular hollow fiber membrane bundle for use in a known oxygenator. It is preferable that the thickness be 5 to 35 mm, particularly 10 mm to 28 mm. Further, a filling rate of the hollow fiber membranes with respect to the tubular space formed by a space between the outside surface of the tubular hollow fiber membrane bundle 22 and the inside surface is not particularly limited, and a filling rate for use in a known oxygenator can be applied similarly. The filling rate is preferably 40% to 85%, particularly 45% to 80%. Furthermore, an outer diameter of the hollow fiber membrane bundle 22 can be an outer diameter similar to an outer diameter of the hollow fiber membrane bundle used in a known oxygenator. The outer diameter of the hollow fiber membrane bundle is preferably 30 to 170 mm, particularly 70 to 130 mm. As a gas exchange membrane, the membrane described above is used.

The hollow fiber membrane bundle 22 can be formed by winding the hollow fiber membranes around the inner tubular member 31, specifically, using the inner tubular member 31 as a core, forming a hollow fiber membrane bobbin, fixing both ends of the formed hollow fiber membrane bobbin by the partition walls, and then cutting both the ends of the hollow fiber membrane bobbin together with the inner tubular member 31 that is a core. The hollow fiber membranes become open on the outside surface of the partition walls by this cutting. A method for forming hollow fiber membranes is not limited to the above method, and any known method for forming hollow fiber membranes may be used similarly or appropriately modified for use.

Particularly, it is preferable that one or a plurality of the hollow fiber membranes be wound around the inner tubular member 31 substantially in parallel at the same time such that adjacent hollow fiber membranes have a substantially constant interval. Therefore, blood drift can be suppressed more effectively. Further, a distance between the hollow fiber membrane and an adjacent hollow fiber membrane is not limited to the following, but the distance is preferably 1/10 to 1/1 of the outer diameter of the hollow fiber membranes. Furthermore, the distance between the hollow fiber membrane and an adjacent hollow fiber membrane is preferably 30 to 200 μm.

Furthermore, preferably, the hollow fiber membrane bundle 22 is formed by one or a plurality (preferably, 2 to 16 membranes) of the hollow fiber membranes being wound around the inner tubular member 31 at the same time such that all adjacent hollow fiber membranes have a substantially constant interval, and the hollow fiber membrane bundle 22 is formed by the hollow fiber membranes being wound around the inner tubular member 31 according to movement of a rotator for rotating the inner tubular member 31 and a winder for interweaving the hollow fiber membranes under the condition in Expression (1) when winding the hollow fiber membranes around the inner tubular member:

traverse[mm/lot]×$n$(integer)=traverse amplitude×2±
(outer diameter of fiber+interval)×the number of windings It is possible to further reduce the formation of blood drift by setting the condition as above. The variable n represents a ratio between the number of rotations of the rotator for winding and the number of reciprocations of the winder at this time, and is not particularly limited, but is usually 1 to 5, preferably 2 to 4.

Further, also in the hollow fiber membrane type oxygenator 20, the antithrombotic polymeric compound 18 according to the present invention coats at least the outer surface 3$a$' (and optionally, the outer surface layer 3$a$) of the hollow fiber membrane 3 of this hollow fiber membrane type oxygenator 1, as shown in FIG. 2. Here, the antithrombotic polymeric compound may exist on the internal layer 3$b$ or the inner surface layer 3$c$ of the hollow fiber membrane 3, but it is preferable that no substantial antithrombotic polymeric compound exist on the internal layer 3$b$ or the inner surface layer 3$c$ of the hollow fiber membrane. Further, the hollow fiber membrane 3 includes, in the center, a passage (lumen) 3$d$ forming the gas chamber. In addition, the hollow fiber membrane 3 includes an opening portion 3$e$ through which the outer surface 3$a$' and the inner surface 3$c$' thereof communicate with each other. Here, the dimensions of the hollow fiber membrane (inner diameter, outer diameter, wall thickness, porosity, size of fine holes, and the like) are not particularly limited, but the same aspect as described in FIG. 1 above can be adopted.

In the oxygenator 20 according to the present embodiment, the hollow fiber membranes 3 have a bobbin shape in which membranes are in contact with each other and overlapped many times. In the present embodiment, the antithrombotic polymeric compound coating is selectively and uniformly formed on the outer surfaces 3$a$' of the hollow fiber membranes. With such a configuration, the leakage of blood (particularly, blood plasma components) to the inner surface layers 3$c$ of the hollow fiber membranes can be suppressed or prevented. That is, the leakage of blood (particularly, blood plasma components) can be effectively suppressed or prevented by the antithrombotic polymeric compound selectively coating the outer surfaces 3$a$' (and optionally, the outer surface layers 3$a$) of the hollow fiber membranes 3, which serve as the blood contact portion. Particularly, in a case where no substantial antithrombotic polymeric compound according to the present invention exists on the internal layers 3$b$ and the inner surface layers 3$c$ of the hollow fiber membranes 3, the hydrophobic state of the material is maintained on the internal layers 3$b$ and the inner surface layers 3$c$ of the hollow fiber membranes, and therefore a large amount of blood (particularly, blood plasma components) leakage can be further effectively suppressed or prevented. In the present embodiment, the blood flow path is complicated and has many narrow portions, which is excellent for the gas exchange capacity, but the adhesion, attachment, and activation of the platelets may deteriorate compared to the oxygenator of an outside blood flow type which is not a bobbin type. However, as described above, since the antithrombotic polymeric compound coating is uniform, the adhesion, attachment, and activation of the platelets in the blood contact portions of the hollow fiber membranes occur less. Furthermore, separation of the coating from the hollow fiber membranes (particularly, a portion where coating is uneven) can be suppressed or prevented.

In addition, it is essential that the antithrombotic polymeric compound coating according to the present embodiment be formed on the outer surfaces of the hollow fiber membranes of the oxygenator. The coating may be formed on another constituent member (for example, on the entire blood contact portion) in addition to the outer surfaces. In the case of having the configuration, adhesion, attachment, and activation of the platelets can be further effectively suppressed or prevented in the entire blood contact portion of the oxygenator. In addition, since a contact angle of the blood contact surface decreases, this can facilitate a priming operation. In this case, it is preferable that the antithrombotic polymeric compound coating be formed on the other constituent member in contact with the blood. The antithrombotic polymeric compound does not coat a portion other than the blood contact portions of the hollow fiber membranes, or on another portion of the hollow fiber membranes (for example, a portion buried in the partition walls, and a contact portion of the hollow fiber). Such a portion is not in contact with the blood, and therefore, the antithrombotic polymeric compound not being coated thereon does not cause a particular problem.

[Method for Manufacturing Oxygenator]

The method for manufacturing an oxygenator according to the present invention includes a method for manufacturing an oxygenator having a hollow fiber membrane bundle with a plurality of porous hollow fiber membranes for gas exchange which have outer surfaces, inner surfaces forming lumens, opening portions through which the outer surfaces communicate with the inner surfaces in a housing, a blood flow path which is outside of the hollow fiber membrane bundle in the housing, a blood inlet port in an upper position of the blood flow path, and a blood outlet port in a lower position of the blood flow path, the method including: filling the blood flow path with a colloidal solution containing an antithrombotic polymeric compound; and moving (circulating) the colloid solution between the blood inlet port and the blood outlet port.

In the method of the present invention, a solution (colloidal solution) containing an antithrombotic polymeric compound is first prepared. Then, the blood flow path is filled with the colloidal solution, and the outer surface of the hollow fiber membrane is coated while moving the colloidal solution. Hereinafter, (1) a step of preparing a colloidal solution and (2) a step of coating (covering) the colloidal solution will be described respectively.

(1) Step of Preparing Colloidal Solution

In this step, a colloidal solution for coating the outer surface of the hollow fiber membrane is prepared. As described above, the colloidal solution used in the method according to the present invention contains an antithrombotic polymeric compound.

First, the antithrombotic polymeric compound used in preparing the colloidal solution according to the present invention will be described.

(Antithrombotic Polymeric Compound and Method for Manufacturing Thereof)

The antithrombotic polymeric compound used in the present invention is a compound that imparts antithrombotic activity to an oxygenator when being applied to the hollow fiber membranes. Further, "the antithrombotic activity" refers to a property of reducing coagulation of blood on a surface that comes into contact with blood.

The antithrombotic polymeric compound can be used without particular limitation as long as it has antithrombotic activity and biocompatibility. Among them, from the viewpoint of the excellent characteristics, the antithrombotic polymeric compound preferably has a structural unit derived from alkoxyalkyl(meth)acrylate represented by the following Formula (I):

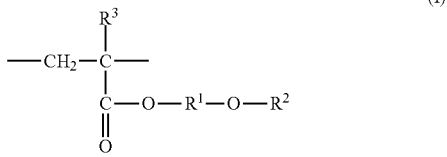

In the formula, $R^3$ represents a hydrogen atom or a methyl group, $R^1$ represents an alkylene group having 1 to 4 carbon atoms, and $R^2$ represents an alkyl group having 1 to 4 carbon atoms.

The compound having a structural unit represented by the Formula (I) is excellent in the antithrombotic activity and biocompatibility (the suppression and prevention effects of adhesion and attachment of the platelets and the suppression and prevention effects of activation of the platelets), particularly excellent in the suppression and prevention effects of activation of the platelets. Therefore, it is possible to manufacture an oxygenator excellent in the antithrombotic activity and biocompatibility (the suppression and prevention effects of adhesion and attachment of the platelets and the suppression and prevention effects of activation of the platelets), particularly excellent in the suppression and prevention effects of activation of the platelets by using the compound having the structural unit.

In the present specification, "(meth)acrylate" means "acrylate and/or methacrylate". That is, "alkoxyalkyl(meth)acrylate" includes all cases of only alkoxyalkyl acrylate, only alkoxyalkyl methacrylate, and alkoxyalkyl acrylate and alkoxyalkyl methacrylate.

In the Formula (I), $R^1$ represents an alkylene group having 1 to 4 carbon atoms. Here, the alkylene group having 1 to 4 carbon atoms is not particularly limited, and includes a linear or branched alkylene group of methylene group, an ethylene group, a trimethylene group, a tetramethylene group, and a propylene group. Among these, an ethylene group and a propylene group are preferable, and in consideration of further enhanced effects of antithrombotic activity and biocompatibility, an ethylene group is particularly preferable. $R^2$ represents an alkyl group having 1 to 4 carbon atoms. Here, the alkyl group having 1 to 4 carbon atoms is not particularly limited, and include a linear or branched alkyl group of a methyl group, an ethyl group, a propyl group, an isopropyl group, a butyl group, an isobutyl group, a sec-butyl group, and a tert-butyl group. Among these, a methyl group and an ethyl group are preferable, and in consideration of further enhanced effects of antithrombotic activity and biocompatibility, a methyl group is particularly preferable. $R^3$ represents a hydrogen atom or a methyl group. Note that in a case where the antithrombotic polymeric compound according to the present invention has two or more of structural units derived from alkoxyalkyl(meth)acrylate, each structural unit may be the same as or different from each other.

Specific examples of alkoxyalkyl(meth)acrylate include methoxymethyl acrylate, methoxyethyl acrylate, methoxypropyl acrylate, ethoxymethyl acrylate, ethoxyethyl acrylate, ethoxypropyl acrylate, ethoxybutyl acrylate, propoxymethyl acrylate, butoxyethyl acrylate, methoxybutyl acrylate, methoxymethyl methacrylate, methoxyethyl methacrylate, ethoxymethyl methacrylate, ethoxyethyl methacrylate, propoxymethyl methacrylate, butoxyethyl methacrylate, and the like. Among these, from the viewpoint of further enhanced effects of antithrombotic activity and biocompatibility, methoxyethyl(meth)acrylate and methoxybutyl acrylate are preferable, and methoxyethyl acrylate (MEA) is particularly preferable. That is, the antithrombotic polymeric compound according to the present invention is preferably polymethoxyethyl acrylate (PMEA). The alkoxyalkyl(meth)acrylate may be used singly, or in mixture of two or more kinds thereof.

The antithrombotic polymeric compound according to the present invention preferably has a structural unit derived from alkoxyalkyl(meth)acrylate, and may be a polymer (homopolymer) having one or two or more of structural units derived from alkoxyalkyl(meth)acrylate, or may be a polymer (copolymer) having one or two or more of structural units derived from alkoxyalkyl(meth)acrylate, and one or two or more of structural units (other structural units) derived from a monomer copolymerizable with the alkoxyalkyl(meth)acrylate. In a case where the antithrombotic polymeric compound according to the present invention is configured to include two or more structural units, the structure of the polymer (copolymer) is not particularly limited, and may be any one of a random copolymer, an alternating copolymer, a periodic copolymer, and a block copolymer. In addition, the end of the polymer is not particularly limited and is appropriately determined according to the type of raw material being used, and is usually a hydrogen atom.

Here, in a case where the antithrombotic polymeric compound according to the present invention has structural units other than the structural units derived from alkoxyalkyl (meth)acrylate, a monomer copolymerizable with the alkoxyalkyl(meth)acrylate (copolymerizable monomer) is not particularly limited. Examples thereof include methyl acrylate, ethyl acrylate, propyl acrylate, butyl acrylate, 2-ethylhexyl acrylate, methyl methacrylate, ethyl methacrylate, propyl methacrylate, butyl methacrylate, 2-ethylhexyl methacrylate, hexyl acrylate, hexyl methacrylate, ethylene, propylene, acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethyl methacrylamide, aminomethyl methacrylate, aminoethyl methacrylate, diaminomethyl methacrylate, diaminoethyl methacrylate, and the like. Among these, as a copolymerizable monomer, a monomer not having a hydroxyl group or a cationic group in the molecule is preferable. The copolymer may be any of a random copolymer, a block copolymer, and a graft copolymer, and can be synthesized by a known method such as radical polymerization, ionic polymerization, or polymerization using a macromer. Here, in all structural units of the copolymer, a ratio of the structural units derived from a copolymerizable monomer is not particularly limited, but in consideration of antithrombotic activity, biocompatibility, and the like, the structural units derived from a copolymerizable monomer (the other structural units) are more than 0% by mole and 50% by mole or less with respect to all structural units of the copolymer. If the units are more than 50% by mole, there is a possibility that the effect of alkoxyalkyl(meth)acrylate deteriorates.

Here, a weight average molecular weight of the antithrombotic polymeric compound is not particularly limited, and is preferably 80,000 or more. In the method for manufacturing an oxygenator according to the present invention, the antithrombotic polymeric compound in the form of the colloidal solution is applied to the outer surface or inner surface of the hollow fiber membrane. Therefore, the weight average molecular weight of the antithrombotic polymeric compound is preferably less than 800,000 from the viewpoint that a desired colloidal solution can be easily prepared. In a case where the weight average molecular weight is within the above range, it is possible to prevent aggregation or precipitation of the compound in the solution containing the antithrombotic polymeric compound and to prepare a stable colloidal solution. Further, the weight average molecular weight of the antithrombotic polymeric compound is preferably more than 200,000 and less than 800,000, more preferably 210,000 to 600,000, still more preferably 220,000 to 500,000, and particularly preferably 230,000 to 450,000.

In the present specification, the "weight average molecular weight" is a weight in which a value measured by gel permeation chromatography (GPC) using polystyrene as a standard substance and tetrahydrofuran (THF) as a mobile phase, is adopted. Specifically, the polymer to be analyzed is dissolved in THF to prepare a 1 mg/ml solution. Regarding the polymer solution thus prepared, a Shodex GPC column LF-804 (manufactured by Showa Denko K.K.) is attached to a GPC system LC-20 (manufactured by Shimadzu Corporation), THF is allowed to flow as a mobile phase, and polystyrene is used as a standard substance to measure GPC of the polymer to be analyzed. After preparing a calibration curve with standard polystyrene, the weight average molecular weight of the polymer to be analyzed is calculated based on this curve.

The content of a polymer having a relatively low molecular weight in the coating can be reduced by increasing the molecular weight of the antithrombotic polymeric compound. As a result, the effects of suppressing or preventing the polymer having a relatively low molecular weight from being eluted into blood is obtained. Therefore, in a case where the weight average molecular weight of the antithrombotic polymeric compound is within the above range, elution of the coating (particularly, a polymer having a low molecular weight) into blood can be further effectively suppressed or prevented. Further, it is also preferable from the viewpoint of antithrombotic activity and biocompatibility. Furthermore, in the present specification, "the polymer having a low molecular weight" means a polymer having a weight average molecular weight of less than 60,000. Note that the method for measuring the weight average molecular weight is as described above.

Further, the antithrombotic polymeric compound having a structural unit derived from alkoxyalkyl(meth)acrylate represented by the Formula (I) can be produced by a known method. Specifically, a method is preferably used, in which alkoxyalkyl(meth)acrylate represented by the following Formula (II):

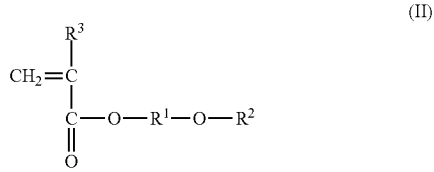

(II)

and one or two or more monomers (copolymerizable monomer) copolymerizable with the above alkoxyalkyl(meth)acrylate added if necessary are stirred in a polymerization solvent together with a polymerization initiator to prepare a monomer solution, and the above monomer solution is heated, whereby alkoxyalkyl(meth)acrylate or alkoxyalkyl(meth)acrylate and a copolymerizable monomer added if necessary are (co)polymerized. In the Formula (II), substituents $R^1$, $R^2$, and $R^3$ are the same as those defined in the Formula (I), and thus description thereof is omitted.

The polymerization solvent that can be used in the preparation of the monomer solution is not particularly limited as long as it is a solvent capable of dissolving the alkoxyalkyl(meth)acrylate of the Formula (II) and a copolymerizable monomer added if necessary. Examples thereof include water, alcohols such as methanol, ethanol, propanol, and isopropanol; aqueous solvents such as polyethylene glycols; aromatic solvents such as toluene, xylene and tetralin; halogenated solvents such as chloroform, dichloroethane, chlorobenzene, dichlorobenzene, trichlorobenzene; and the like. Among these, in consideration of alkoxyalkyl(meth)acrylate being easily dissolved and the polymer that has the above weight average molecular weight being easily obtained, methanol is preferable.

A monomer concentration in the monomer solution is not particularly limited, but the weight average molecular weight of the antithrombotic polymeric compound obtained can be increased by setting the concentration relatively high. For this reason, in consideration of the polymer that has the weight average molecular weight being easily obtained, and the like, the monomer concentration in the monomer solution is preferably less than 50% by mass, and more preferably 15% by mass or more and less than 50% by mass. Further, the monomer concentration in the monomer solution is preferably 20% by mass or more and 48% by mass or less, and particularly preferably 25% by mass or more and 45% by mass or less. In a case of using two or more of monomers, the monomer concentration means a total concentration of these monomers.

The polymerization initiator is not particularly limited, and a known initiator may be used. The initiator is a radical polymerization initiator in terms of being excellent in polymerization stability, and examples thereof include persulfates such as potassium persulfate (KPS), sodium persulfate and ammonium persulfate; peroxides such as hydrogen peroxide, t-butyl peroxide and methyl ethyl ketone peroxide; and azo compounds such as azobisisobutyronitrile (AIBN), 2,2'-azobis(4-methoxy-2,4-dimethylvaleronitrile), 2,2'-azobis(2,4-dimethylvaleronitrile), 2,2'-azobis[2-(2-imidazolin-2-yl)propane]dihydrochloride, 2,2'-azobis[2-(2-imidazolin-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1,1-dimethylbutyl peroxyneodecanoate, a-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(secondary butyl)peroxydicarbonate, and azobiscyanovaleric acid. For example, a reducing agent such as sodium sulfite, sodium hydrogen sulfite or ascorbic acid may be used in combination with the radical polymerization initiators as a redox type initiator. A blending amount of the polymerization initiators is preferably 0.0001% to 1% by mole, more preferably 0.001% to 0.8% by mole, and particularly preferably 0.01% to 0.5% by mole with respect to a total amount of the monomer (alkoxyalkyl(meth)acrylate and a copolymerizable monomer added if necessary; hereinafter the same applies). Alternatively, the blending amount of the polymerization initiators is preferably 0.005 to 2 parts by mass, and more preferably 0.05 to 0.5 parts by mass with respect to 100 parts by mass of monomer (a total mass in a case of using a plurality of types of monomers). With such a blending amount of the polymerization initiators, the polymer having a desired weight average molecular weight can be more efficiently produced.

The polymerization initiator may be directly mixed with the monomers and the polymerization solvent. The initiator in a solution state obtained by the initiator dissolved in another solvent in advance, may be directly mixed with the monomers and the polymerization solvent. In the latter case, the solvent is not particularly limited, as long as the polymerization initiator can be dissolved in the solvent, and can be, for example, a solvent similar to the above polymerization solvent. Further, the solvent may be the same as or different from the above polymerization solvent, but is preferably a solvent that is the same as the above polymerization solvent in consideration of the ease of control of polymerization. Furthermore, in this case, a concentration of the polymerization initiator in the solvent is not particularly limited, but an addition amount of the polymerization initiator is preferably 0.1 to 10 parts by mass, more preferably, 0.15 to 5 parts by mass, still more preferably 0.2 to 1.8 parts by mass with respect to 100 parts by mass of the solvent in consideration of the ease of mixing, and the like.

Next, the above monomer solution is heated, and thus alkoxyalkyl(meth)acrylate or alkoxyalkyl(meth)acrylate and the other monomer are (co)polymerized. Here, as a polymerization method, for example, a known polymerization method such as radical polymerization, anionic polymerization, and cationic polymerization can be adopted, and radical polymerization which facilitates production is preferably used.

Polymerization conditions are not particularly limited, as long as the above monomers (alkoxyalkyl(meth)acrylate or alkoxyalkyl(meth)acrylate and the copolymerizable monomer) can be polymerized under the conditions. Specifically, the polymerization temperature is preferably 30° C. to 60° C., and more preferably 40° C. to 55° C. Further, the polymerization time is preferably 1 to 24 hours, and more preferably 3 to 12 hours. Under such conditions, a polymer having a high molecular weight as described above can be further efficiently produced. In addition, it is possible to effectively suppress or prevent gelation in the polymerization process and to achieve high production efficiency.

In addition, a chain transfer agent, a polymerization rate-adjusting agent, a surfactant, and other additives may be appropriately used during polymerization if necessary.

An atmosphere under which the polymerization reaction is carried out is not particularly limited, and the reaction may be carried out under an air atmosphere, an inert gas atmosphere such as nitrogen gas or argon gas, and the like. In addition, during the polymerization reaction, the reaction solution may be stirred.

The polymer after polymerization can be purified by a general purification method such as a reprecipitation method, a dialysis method, an ultrafiltration method or an extraction method. For the reason that a (co)polymer suitable for preparing the colloidal solution can be obtained, it is preferable to perform purification by a reprecipitation method among the above. Ethanol is preferably used as a poor solvent used for performing reprecipitation.

The purified polymer can be dried by an arbitrary method such as freeze drying, reduced pressure drying, spray drying or heat drying, but freeze drying or reduced pressure drying is preferable from the viewpoint that the influence on the physical properties of the polymer is small.

Subsequently, a method for preparing a colloidal solution according to the present invention will be described.

Preparation of Colloidal Solution

A solvent used in preparation of the antithrombotic polymeric compound-containing solution (colloidal solution) is not particularly limited, as long as it can appropriately disperse the antithrombotic polymeric compound to prepare the colloidal solution. Preferably, the solvent contains water to further effectively reduce or prevent the penetration of the colloidal solution to the outer surfaces or the inner surfaces of the fine holes of the hollow fiber membranes (a surface on the side where the oxygen-containing gas flows). Here, water is preferably pure water, ion exchange water or distilled water, and among these, pure water (RO water) purified by a reverse osmosis membrane is preferable.

A solvent other than water, which is used in preparation of the colloidal solution, is not particularly limited, but is preferably methanol or acetone in consideration of further ease of controlling dispersibility of the antithrombotic polymeric compound, and the like. The above solvent other than water may be used singly, or in mixture of two or more kinds thereof. Among these, in consideration of further ease of controlling dispersibility of the antithrombotic polymeric compound, and the like, the solvent is preferably methanol. That is, the solvent preferably contains water and methanol. Here, a mixing ratio of water and methanol is not particularly limited. In consideration of dispersibility of the antithrombotic polymeric compound and further ease of controlling an average particle size of the colloid particles, the mixing ratio (mass ratio) of water:methanol is preferably 6:1 to 32:1, and more preferably 10:1 to 30:1. That is, the solvent preferably contains water and methanol in the mixing ratio (mass ratio) of 6:1 to 32:1, and more preferably contains water and methanol in the mixing ratio (mass ratio) of 10:1 to 30:1.

As described above, when preparing the colloidal solution by using a mixed solvent of water and a solvent other than water, the order of adding the solvent (for example, water and methanol) and the antithrombotic polymeric compound is not particularly limited. It is preferable to prepare the colloidal solution in the following order. That is, preferably, the antithrombotic polymeric compound is added to a solvent other than water (preferably, methanol) to prepare the antithrombotic polymeric compound-containing solution, and then the colloidal solution is prepared by a method of adding the antithrombotic polymeric compound-containing solution to water. The antithrombotic polymeric compound is easily dispersed by such a method. Further, the above method has an advantage that colloid particles having a uniform particle size can be formed, and a uniform coating can be easily formed.

In the above method, an addition rate of the antithrombotic polymeric compound-containing solution to water is not particularly limited, but it is preferable to add the antithrombotic polymeric compound-containing solution to water at an addition rate of 10 to 10,000 g/min.

Stirring time and stirring temperature in preparation of the colloidal solution are not particularly limited. From the viewpoint of forming the colloid particles having a uniform particle size and ease of dispersing the colloid particles uniformly, it is preferable to perform stirring for 1 to 30 minutes, and is more preferable to perform stirring for 5 to 15 minutes, after addition of the antithrombotic polymeric compound to water. Further, the stirring temperature is preferably 10° C. to 40° C., and more preferably from 20° C. to 30° C.

A concentration of the antithrombotic polymeric compound in the colloidal solution is not particularly limited. From the viewpoint of ease of increasing the coating amount, the concentration is preferably 0.005% by mass or more. Further, from the above viewpoint, the colloidal solution contains the antithrombotic polymeric compound, preferably at a concentration of 0.01% by mass or more, more preferably at a concentration of 0.03% by mass or more, and particularly preferably at a concentration of 0.04% by mass or more. On the other hand, an upper limit of a concentration of the antithrombotic polymeric compound in the colloidal solution is not particularly limited. In consideration of ease of forming the coating and the effect of reducing coating unevenness, the concentration is preferably 0.3% by mass or less, and more preferably 0.2% by mass or less. Furthermore, in such a range, a decrease in gas exchange capacity due to an excessively thick coating of the antithrombotic polymeric compound is also suppressed.

(2) Step of Colloidal Solution Coating (Applying)

Next, the outer surfaces of the hollow fiber membranes are coated with the colloidal solution prepared in the above manner. Specifically, after assembling an oxygenator (for example, an oxygenator having the same structure as that of FIG. 1 or FIG. 3), the blood flow path is filled with the colloidal solution prepared in the above step (1), and the colloidal solution is moved (e.g., circulated) between the blood inlet port and the blood outlet port, whereby the outer surfaces of the hollow fiber membranes are coated with the antithrombotic polymeric compound.

Here, a method of moving the colloidal solution between the blood inlet port and the blood outlet port is not particularly limited, and examples thereof include a method of circulating the colloidal solution into the blood flow path of the oxygenator and a method of moving the colloidal solution back and forth (i.e., a reciprocating motion) between the blood inlet port and the blood outlet port. Among these, the method of moving the colloidal solution back and forth between the blood inlet port and the blood outlet port is preferable from the viewpoint of equipment cost.

The method of circulating the colloidal solution into the blood flow path of the oxygenator is not particularly limited as long as it is a method in which the colloidal solution can be circulated. For example, a roller pump is used to circulate the colloidal solution to the blood flow path of the oxygenator at a constant flow rate. In this case, a flow rate of the colloidal solution in the blood flow path is preferably 0.1 L/min or more, more preferably 1 L/min or more, and still more preferably 3 L/min or more. When the flow rate is within this range, the time required for the coating step can be reduced. Further, the flow rate of the colloidal solution in the blood flow path is preferably 10 L/min or less, more preferably 8 L/min or less, and still more preferably 5 L/min or less. When the flow rate is within this range, the roller pump can be used, so this is preferable. Circulation time of the colloidal solution in the blood flow path is not particularly limited, and the circulation time can be appropriately adjusted according to the flow rate. From the viewpoint of the time required for the coating step and the balance of the coating amount, the circulation time of the colloidal solution circulating in the blood flow path is preferably 1 minute or more and 1 hour or less, more preferably 3 minutes or more and 30 minutes or less, and still more preferably 5 minutes or more and 10 minutes or less.

The method of moving the colloidal solution back and forth between the blood inlet port and the blood outlet port is not particularly limited as long as it is possible to move the colloidal solution back and forth. For example, tubes are connected to the blood inlet port and the blood outlet port of the oxygenator, the tube connected to the blood inlet port or the blood outlet port is interposed between two pressing plates, and the pressing plates are moved back and forth by a motor, so that it is possible to move the colloidal solution in the blood flow path back and forth. In this case, a flow rate of the colloidal solution moving back and forth can be controlled by adjusting the inner diameter of the tube, the length of the pressing plate, or the frequency at which the pressing plate moves back and forth. An inner diameter of the tube is not particularly limited, but the inner diameter is preferably 3.0 mm or more, more preferably 5.0 mm or more, and still more preferably 9.0 mm or more. Further, the inner diameter of the tube is preferably 20.0 mm or less, more preferably 15 mm or less, and still more preferably 11.0 mm or less. When the inner diameter is within the above range, a speed of the colloidal solution moving back and forth can be easily adjusted. Further, the shape and material of the pressing plate are not particularly limited. A plate-like or cylindrical pressing plate may be used. Further, a pressing plate made of metal such as aluminum or iron may be used. From the viewpoint of ease of controlling the flow rate of the colloidal solution, a plate-like pressing plate is preferably used. In addition, the plate made of aluminum is more preferably used from the viewpoint of availability of materials. In a case where the plate-like pressing plate is used, it is possible to control the flow rate of the colloidal solution moving back and forth by adjusting the length of the pressing plate. At this time, when the length of the pressing plate is long, a larger amount of the colloidal solution can be moved back and forth in the blood flow path by one forward and backward movement of the pressing plate. From this viewpoint, the length of the pressing plate is preferably 10 mm or more, more preferably 30 mm or more, and still more preferably 60 mm or more. Further, when the length of the pressing plate is short, the coating step can proceed smoothly. From this viewpoint, the length of the pressing plate is preferably 200 mm or less, more preferably 160 mm or less, and still more preferably 120 mm or less. Further, a frequency at which the pressing plate moves back and forth is preferably 0.5 to 5 back-and-forth movements per second, more preferably 1 to 4 back-and-forth movements per second, and more preferably 2 to 3 back-and-forth movements per second. When the frequency is within the above range, the efficiency and smoothness of the coating step can be balanced. The flow rate of the colloidal solution moving back and forth in the blood flow path can be appropriately adjusted, and optimization conditions for improving the coating amount can be achieved. Further, when the colloidal solution is moved back and forth between the blood inlet port and the blood outlet port, an amount of the colloidal solution to be moved is not particularly limited, but is preferably 1 L/min·m$^2$ or more and 10 L/min·m$^2$ or less, preferably 2 L/min·m$^2$ or more and 8 L/min·m$^2$ or less, and more preferably 3 L/min·m$^2$ or more and 5 L/min·m$^2$ or less with respect to the membrane area (m$^2$) of the hollow fiber membrane. The colloidal solution is moved at the above rate, whereby the adsorption of the colloid particles to the surface of the hollow fiber membrane proceeds favorably, the coating amount is sufficient, and the coating unevenness can be reduced.

In the present specification, "the membrane area" refers to an area of the outer surface of the hollow fiber membrane, and is calculated from the product of the outer diameter, the circumference ratio, the number, and the effective length of the hollow fiber membrane.

The moving time of the colloidal solution is also not particularly limited, but is preferably 30 seconds or more and 100 minutes or less, more preferably 1 minute or more and 70 minutes or less, and still more preferably 1 minute or more and 30 minutes or less in consideration of the coating amount, the ease of forming the coated film, and the effect of reducing coating unevenness. In addition, a contact temperature of the colloidal solution and the hollow fiber membrane (circulation temperature of the colloidal solution to the blood flowing side of the oxygenator) is preferably 5° C. to 40° C., and more preferably 15° C. to 30° C. in consideration of the coating amount, the ease of forming the coated film, and the effect of reducing coating unevenness.

In one embodiment of the present invention, in the method for manufacturing an oxygenator, preferably, the lumens of the hollow fiber membranes are used as a gas flow path, and carbon dioxide gas is passed through the gas flow path while simultaneously moving the colloidal solution between the blood inlet port and the blood outlet port. Thus, the aggregation of the colloid particles in the colloidal solution and the adsorption of the colloid particles to the outer surface of the hollow fiber membrane further progress. A mechanism is presumed as follows. That is, it is considered that the colloid particles (surfaces of particles) of the antithrombotic polymeric compound contained in the colloidal solution are negatively charged, and cations exist around the colloid particles so as to neutralize this charge. In other words, it is assumed that the colloid particles are in a state of forming an electric double layer. A theory of electrostatic repulsion based on the electric double layer is known as the Derjaguin-Landau-Verwey-Overbeek (DLVO) theory. According to this theory, the total potential energy of the force acting between the colloid particles is the sum of the potential energy of the electric repulsion and the potential energy of the van der Waals attraction. In order to allow the particles to aggregate close together, the particles need to cross a peak of total potential energy. If the peak of potential energy is much higher than a thermal kinetic energy of the particles, it is not possible to exceed the peak. Therefore, even if the particles approach, the particles are repulsed and do not aggregate, and the colloid is stable. The electric repulsion is stronger as the thickness of the electric double layer is larger. However, as the electrolyte concentration in the solution is higher, the diffusion layer is compressed and the thickness of the electric double layer is reduced. Therefore, when carbon dioxide gas is blown into a colloidal solution containing colloid particles having an electric double layer, carbon dioxide is dissolved in water, and hydrogen carbonate ions ($HCO_3^-$), carbonate ions ($CO_3^{2-}$), and hydrogen ions ($H^+$) are generated. The thickness of the electric double layer is reduced and the electric repulsion is reduced, whereby the colloid particles easily aggregate. At this time, a similar phenomenon occurs not only between the colloid particles but also between the outer surface of the hollow fiber membrane and the colloid particles, and it is considered that the colloid particles are likely to be adsorbed on the outer surface of the hollow fiber membrane.

The flow rate of carbon dioxide gas is not particularly limited, but is preferably 0.5 L/min·m$^2$ or more and 20 L/min·m$^2$ or less, more preferably 1 L/min·m$^2$ or more and 10 L/min·m$^2$ or less, and still more preferably 2 L/min·m$^2$ or more and 5 L/min·m$^2$ or less with respect to the membrane area (m$^2$) of the hollow fiber membrane. The carbon dioxide gas is circulated at the above rate, whereby the aggregation of the colloid particles and the adsorption of the colloid particles to the outer surface of the hollow fiber membrane proceed favorably, the coating amount is sufficient, and the coating unevenness can be reduced. In the present specification, a volume (L) of carbon dioxide gas means a volume at 25° C. and 1 atm.

When circulating the carbon dioxide gas, another gas (for example, an inert gas such as nitrogen gas) may be circulated in addition to the carbon dioxide gas. However, it is preferable that a ratio of the gas be smaller than a ratio of the carbon dioxide gas from the viewpoint of obtaining an oxygenator with a sufficient coating amount and less coating unevenness. Specifically, a circulation amount (volume) of the gas is preferably 0% by volume or more and 50% by volume or less, more preferably 0% by volume or more and 20% by volume or less, and most preferably 0% by volume with respect to a circulation amount (volume) of the carbon dioxide gas.

After coating the hollow fiber membrane with the above colloidal solution, the coated film is dried to form a coat (coating) of the antithrombotic polymeric compound of the present invention on the outer surfaces of the hollow fiber membranes. Here, a drying condition is not particularly limited, as long as it is a condition where the coat (coating) of the antithrombotic polymeric compound according to the present invention can be formed on the outer surfaces (and optionally, on the outer surface layers) of the hollow fiber membranes. Specifically, a drying temperature is preferably from 5° C. to 50° C., and more preferably from 15° C. to 40° C. Further, drying time is preferably 60 to 300 minutes, and more preferably 120 to 240 minutes. Alternatively, the coated film may be dried by continuously or gradually flowing gas preferably at 5° C. to 40° C., more preferably at 15° C. to 30° C., into the hollow fiber membranes. Here, the types of the gas are not particularly limited as long as a gas has no influence on the coated film and the coated film can be dried thereby. Specific examples thereof include air, an inert gas such as nitrogen gas, argon gas, and the like. A circulation amount of the gas is not particularly limited as long as it is an amount at which the coated film can be sufficiently dried, but is preferably 5 to 150 L/min, more preferably 30 to 100 L/min, and still more preferably 50 to 90 L/min.

The method for manufacturing an oxygenator according to the present invention is used, so that it is possible to manufacture a hollow fiber membrane oxygenator of an outside blood flow type that has a coating containing a sufficient amount of the antithrombotic polymeric compound on the outer surfaces of the hollow fiber membranes (hereinafter, simply referred to as "oxygenator"). According to the method for manufacturing a hollow fiber membrane oxygenator of an outside blood flow type, there is also provided a hollow fiber membrane oxygenator of an outside blood flow type that has a coating on outer surfaces of the hollow fiber membranes containing the antithrombotic polymeric compound in an amount of 5 mg/m$^2$ surface or more and 100 mg/m$^2$ surface or less. An amount of the antithrombotic polymeric compound in the coating is more preferably 10 mg/m$^2$ surface to 60 mg/m$^2$ surface, and still more preferably 15 mg/m$^2$ surface to 50 mg/m$^2$ surface. When the coating amount of the antithrombotic polymeric compound is 5 mg/m$^2$ or more, an oxygenator having excellent antithrombotic activity can be obtained. On the other hand, an upper limit of a coating amount is not particularly limited, but is preferably 100 mg/m$^2$ or less. When the coating amount is such a value, a decrease in the gas exchange capacity due to an excessively thick coating containing the antithrombotic polymeric compound is suppressed, and an oxygenator having excellent in gas exchange capacity can be obtained. As the above coating amount, a value measured by a method described in the following examples is employed.

As described above, the oxygenator according to the present invention is coated with a sufficient amount of the antithrombotic polymeric material, so that the antithrombotic activity on the outer surface side of the hollow fiber membrane is improved. Therefore, when the oxygenator is incorporated into the extracorporeal circuit and the blood is circulated, a platelet count maintenance rate of the circulated blood is improved. Specifically, the platelet count maintenance rate after circulating the blood for 30 minutes is preferably more than 70%, more preferably 80% or more, and particularly preferably 90% or more (upper limit: 100%).

EXAMPLES

Effects of the present invention will be explained using the following examples and a comparative example. However, the technical scope of the present invention is not limited only to the following examples. In the following examples, operation was performed at room temperature (25° C.) unless otherwise specified. In addition, unless otherwise specified, "%" and "parts" mean "% by mass" and "parts by mass", respectively.

Synthesis of Antithrombotic Polymeric Compound

Preparation Example 1: Synthesis of PMEA Having Weight Average Molecular Weight of 350,000

35 g (0.27 mol) of 2-methoxyethyl acrylate (MEA) was dissolved in 160 g of methanol and put in a 4-necked flask, and $N_2$ bubbling was carried out at 50° C. for 1 hour to prepare a monomer solution. Additionally, 0.035 g of 2,2'-azobis(4-methoxy-2,4-dimethylvaleronitrile) (V-70, manufactured by Wako Pure Chemical Industries, Ltd.) was dissolved in 5 g of methanol to prepare a polymerization initiator solution. Next, this polymerization initiator solution was added to the monomer solution, and the polymerization reaction was carried out at 50° C. for 5 hours. After polymerization for a predetermined time, the polymerization solution was added dropwise to ethanol, and the precipitated polymer (PMEA) was recovered. When a weight average molecular weight of the recovered polymer was measured, the weight was 350,000.

Preparation of Colloidal Solution

Example 1-1: Colloidal Solution Having PMEA Concentration of 0.04% by Mass 0.48 g of PMEA (weight average molecular weight=350,000) synthesized in Preparation Example 1 was dissolved in 48 g of methanol. To another container, 1140 g of RO water was added, and the methanol solution of PMEA as described above was added at an addition rate of 2400 g/min. Thereafter, the mixture was stirred at 25° C. for 3 minutes to obtain a white turbid colloidal solution. The colloidal solution was a colloidal solution in which the colloid of PMEA was dispersed.

Production of Oxygenator

A hollow fiber membrane oxygenator of an outside blood flow type that has a membrane area (area of the outer surfaces of the hollow fiber membranes) of 0.5 $m^2$ was produced, and the oxygenator is wound around by porous hollow fiber membranes for gas exchange made of porous polypropylene having an inner diameter of 195 μm, an outer diameter of 295 μm, a wall thickness of 50 μm, a porosity of about 35% by volume, and a hole size of the outer surfaces (that is, an average diameter of the opening portions) of 80 nm are wound.

Example 1

Tubes (inner diameter 9.5 mm×outer diameter 14.2 mm) were connected to the blood inlet port and the blood outlet port of the above oxygenator, and the tube connected to the blood inlet port was interposed between two aluminum plates. 96 g of the colloidal solution prepared as above was put in the tubes in the oxygenator, and the end of the tube connected to the blood inlet port was clamped. While flowing carbon dioxide gas from the gas inlet port to the gas outlet port of the oxygenator at a flow rate of 4 L/min·$m^2$ from the gas port, one of the aluminum plates (length: 91 mm) was moved back and forth by a motor with 2 back-and-forth movements per second. Then, the colloidal solution was moved back and forth for 1 minute. The closest distance between the two aluminum plates was 4.5 mm. At this time, the amount of the moved colloidal solution was 3 L/min·$m^2$ with respect to the membrane area ($m^2$) of the hollow fiber membrane. The tubes were removed from the oxygenator and the liquid was drained and collected. Then, air was blown at 80 L/min to further collect the liquid. The drying was continued while the air was kept flowing.

Measurement of Concentration of Carbon Dioxide GAS in Colloidal Solution

Since the colloidal solution and water are considered to dissolve carbon dioxide gas to the same extent, instead of measuring a concentration of carbon dioxide gas in the colloidal solution, a concentration of carbon dioxide gas in water under the same conditions was measured.

First, 500 ml of RO water was put into a beaker, carbon dioxide gas was bubbled at 2 L/min, and a partial pressure of carbon dioxide gas was measured with a blood gas analyzer and the conductivity was measured with a conductivity meter. Then, the conductivity was plotted on the horizontal axis and the partial pressure of carbon dioxide gas was plotted on the vertical axis, and then the approximate Expression (2) was obtained:

partial pressure of carbon dioxide gas(mmHg)
=18.587×conductivity(μs/cm)−237.63

200 ml of RO water was put into a closed circuit including a hollow fiber membrane oxygenator of an outside blood flow type, a bag made of vinyl chloride, and a tube, and carbon dioxide gas was circulated from the gas inlet port to the gas outlet port of the hollow fiber membrane oxygenator of an outside blood flow type at 2 L/min (4 L/min·$m^2$). RO water before circulation and RO water 5 minutes after the start of circulation were sampled and measured with the blood gas analyzer and the conductivity meter.

The RO water before circulation could not be measured because the concentration of carbon dioxide gas was below the measurement lower limit (5 mmHg) of the blood gas analyzer. In addition, RO water 5 minutes after the start of circulation could not be measured because the concentration of carbon dioxide gas exceeded the measurement upper limit (250 mmHg), but the conductivity was 42.1 µS/cm, so the partial pressure of carbon dioxide gas was calculated as 544 (mmHg) from Expression 1.

From the above results, it is considered that the concentration of carbon dioxide gas in the coating liquid is 5 mmHg or less in a case where no carbon dioxide gas flows, and about 544 (mmHg) in a case where the carbon dioxide gas flows, similarly to the concentration of carbon dioxide gas in water.

Measurement of Coating Amount

The housing of the oxygenator was cut and disassembled with an ultrasonic disc cutter, and the hollow fiber membrane was cut with a cutter. A total amount of the hollow fiber membranes was put into a glass bottle with a cap, acetone was added, and the mixture was extracted with an ultrasonic cleaner for 1 hour. 46 g of the acetone extract was collected in another glass bottle with a cap, and acetone was evaporated by heat block. Then, the evaporated and dried product was dissolved in 10 mL of tetrahydrofuran. The dissolved colloidal solution was shaken for 1 hour with a shaker, and dissolved for 1 hour with an ultrasonic cleaner. The resultant colloidal solution was filtrated through a 0.45 µm filter, and the filtrate was quantified by gel permeation chromatography (GPC). Specifically, a THF solution (standard solution) containing 1 mg/mL of PMEA was analyzed using GPC, and an area of a peak corresponding to PMEA was calculated. Subsequently, a THF solution (test solution) of the evaporated and dried product was analyzed using GPC, and an area of a peak corresponding to PMEA was calculated in the same manner as described above. Thereafter, the amount of PMEA in the test solution was calculated using the following Expression (3), and the coating amount of PMEA per 1 m² of the membrane of the oxygenator (an area of the outer surface of the hollow fiber membrane: 1 m²) was calculated using Expression (5).

amount of PMEA in test solution (mg)=(area of peak of test solution/area of peak of standard solution)×10           Expression (3):

total amount of PMEA(mg)=amount of PMEA in test solution(mg)×(total amount of acetone/amount of recovered acetone)           Expression (4):

coating amount of PMEA on oxygenator (mg/m²) =total amount of PMEA/(weight of oxygenator subjected to extraction×area of membrane per 1 g of oxygenator)           Expression (5):

Colloid Use Efficiency

After the coating, part (32 mL) of the colloidal solution was discharged, and the discharged colloidal solution was dried by heat block and vacuum drying, and then dissolved in 1.5 mL of tetrahydrofuran. The dissolved colloidal solution was shaken for 1 hour with a shaker, and dissolved for 1 hour with an ultrasonic cleaner. The resultant colloidal solution was filtrated through a 0.45 pm filter, and the filtrate was quantified by gel permeation chromatography (GPC). Specifically, the amount of PMEA in the discharged colloidal solution was calculated by the same method as in Expression (3) as described above. Thereafter, the amount of PMEA in the whole colloidal solution after coating was calculated using the following Expression (6), and the colloid use efficiency was calculated using the following Expression (7).

amount of PMEA in whole colloidal solution after coating(mg)=amount of PMEA in discharged colloidal solution×(amount of whole colloidal solution/amount of discharged colloidal solution)           Expression (6):

colloid use efficiency=(1−(amount of PMEA in whole colloidal solution after coating/ amount of PMEA in whole colloidal solution before coating))×100 (%)           Expression (7):

Example 2

Tubes (inner diameter 9.5 mm×outer diameter 14.2 mm) were connected to the blood inlet port and the blood outlet port of the above oxygenator, and the tube connected to the blood inlet port was interposed between two aluminum plates. The above colloidal solution was put in the tubes in the oxygenator, and the end of the tube connected to the blood inlet portion was clamped. Without using carbon dioxide, one of the aluminum plates (length: 91 mm) was moved back and forth by the motor with 2 back-and-forth movements per second, whereby the coating liquid was moved back and forth for 1 minute. The closest distance between the two aluminum plates was 4.5 mm. The tubes were removed from the oxygenator and the liquid was drained and collected. Then, air was blown at 80 L/min to further collect the liquid. The drying was continued while the air was kept flowing.

The measurement of the coating amount and the measurement of the colloid use efficiency were performed in the same manner as in Example 1.

Comparative Example

Tubes (inner diameter 9.5 mm×outer diameter 14.2 mm) were connected to the blood inlet port and the blood outlet port of the above oxygenator. The colloidal solution was put in the tubes in the oxygenator, and the coating liquid was held (without movement) for 1 minute. The tubes were removed from the oxygenator and the liquid was drained and collected. Then, air was blown at 80 L/min to further collect the liquid. The drying was continued while the air was kept flowing.

The measurement of the coating amount and the measurement of the colloid use efficiency were performed in the same manner as in Example 1.

Figure 8:
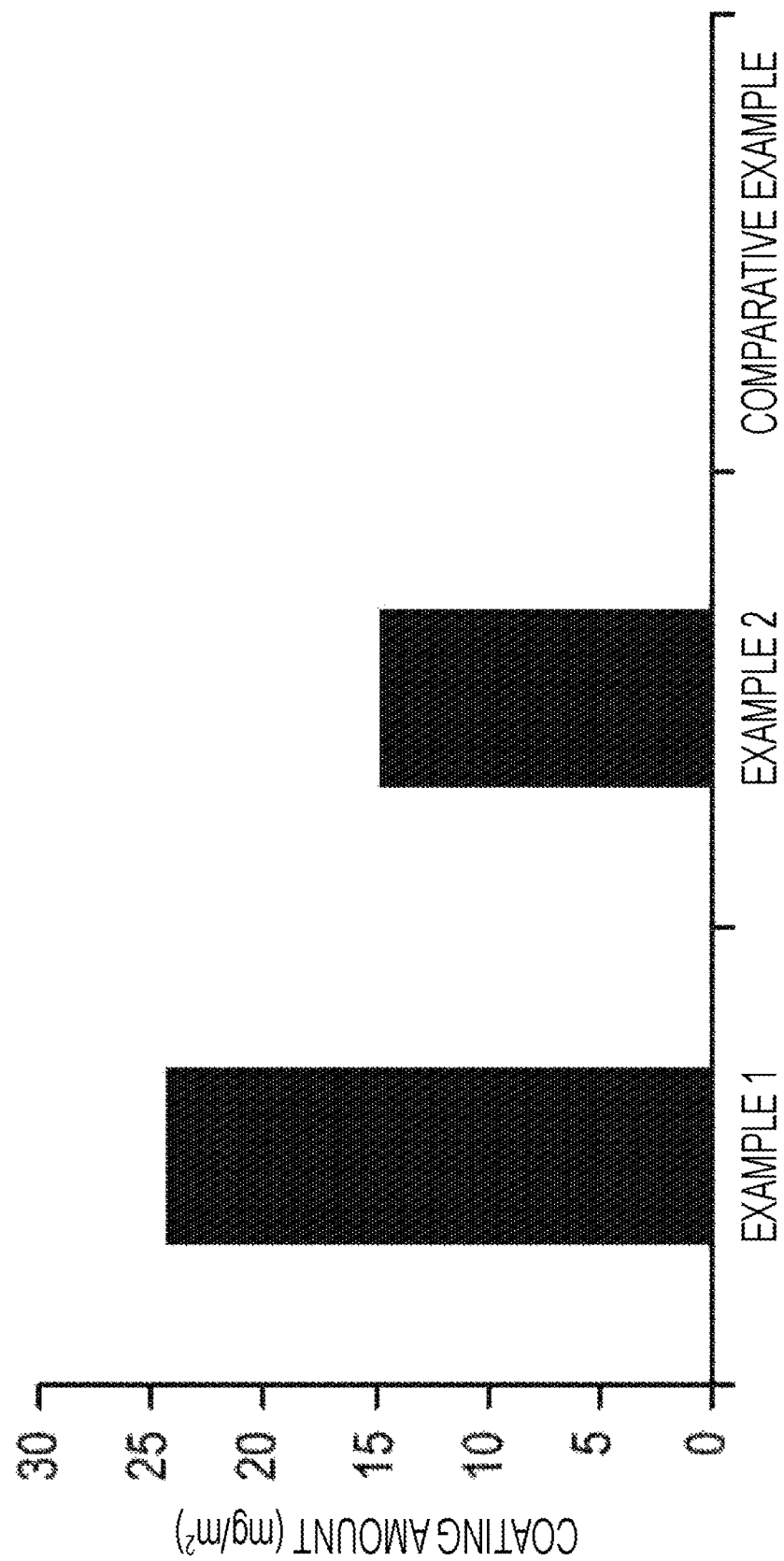
FIG. 8 is a graph showing coating amounts in Examples of the invention and a Comparative Example.

The measurement results of the coating amount are shown in FIG. 8, and the measurement results of the colloid use efficiency are shown in FIG. 9. In Examples 1 and 2, it was found that the colloid use efficiency was improved and the coating amount of the colloidal solution on the hollow fiber was increased as compared with the comparative example. Further, among the examples, the colloid use efficiency of Example 1 is further increased. This can be presumed to be due to the fact that the movement of the coating liquid increased the colloid use efficiency, and the addition of carbon dioxide further increased the colloid use efficiency.

What is claimed is:

1. A method for manufacturing an oxygenator having a housing retaining a hollow fiber membrane bundle, wherein the hollow fiber membrane bundle comprises a plurality of porous hollow fiber membranes for gas exchange which have outer surfaces, inner surfaces forming lumens, and opening portions through which the outer surfaces communicate with the inner surfaces, wherein the oxygenator defines a blood flow path which is outside of the hollow fiber membranes in the housing between a blood inlet port and a blood outlet port, the method comprising:

filling the blood flow path with a colloidal solution containing an antithrombotic polymeric compound; and moving the colloidal solution along the blood flow path between the blood inlet port and the blood outlet port for a time that coats a predetermined amount of antithrombotic polymeric compound on the outer surfaces of the hollow fiber membranes, wherein the colloidal solution is moved alternately back and forth between the blood inlet port and the blood outlet port.

2. The method for manufacturing an oxygenator according to claim 1, wherein the colloidal solution is supplied to the blood flow path by a tube, wherein the tube is interposed between two pressing plates, and wherein the pressing plates are moved back and forth by a motor.

3. The method for manufacturing an oxygenator according to claim 1, wherein the colloidal solution is moved alternately back and forth by a pump coupled to the blood inlet port and the blood outlet port.

4. The method for manufacturing an oxygenator according to claim 1, wherein the colloidal solution is moved back and forth at a rate of from 0.5 to 5 back-and-forth movements per second.

5. The method for manufacturing an oxygenator according to claim 1, wherein a flow rate of the colloidal solution is between 1 L/min·m$^2$ and 10 L/min·m$^2$.

6. The method for manufacturing an oxygenator according to claim 1, wherein the colloidal solution contains 0.01% by mass or more of an antithrombotic polymeric compound.

7. The method for manufacturing an oxygenator according to claim 1, wherein the antithrombotic polymeric compound has a structural unit derived from alkoxyalkyl(meth)acrylate represented by the following Formula (I):

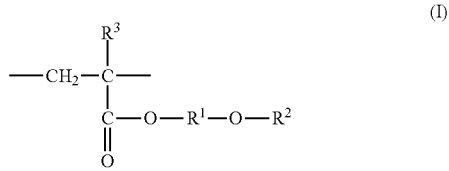

(I)

wherein $R^3$ represents a hydrogen atom or a methyl group, $R^1$ represents an alkylene group having 1 to 4 carbon atoms, and $R^2$ represents an alkyl group having 1 to 4 carbon atoms.

8. The method for manufacturing an oxygenator according to claim 1, wherein a weight average molecular weight of the antithrombotic polymeric compound is more than 200,000 and less than 800,000.

9. A method for manufacturing an oxygenator for an extracorporeal blood circulator, comprising the steps of:

assembling a housing and a hollow fiber membrane bundle, wherein the housing comprises a blood inlet port, a blood outlet port, and housing surfaces for defining a blood flow path in an inner chamber, wherein the hollow fiber membrane bundle is retained in the inner chamber and comprises a plurality of porous hollow fiber membranes for gas exchange which have outer surfaces, inner surfaces forming lumens, and opening portions through which the outer surfaces communicate with the inner surfaces in a housing, and wherein the blood flow path passes over the outer surfaces of the hollow fiber membranes in the inner chamber;

filling the blood flow path with a colloidal solution containing an antithrombotic polymeric compound; and moving the colloidal solution along the blood flow path between the blood inlet port and the blood outlet port for a time that coats a predetermined amount of antithrombotic polymeric compound on the outer surfaces of the hollow fiber membranes, wherein the colloidal solution is moved alternately back and forth between the blood inlet port and the blood outlet port.

10. The method of claim 9 wherein moving the colloidal solution further coats the antithrombotic polymeric compound on the housing surfaces, and wherein the colloidal solution is moved back and forth at a rate of from 0.5 to 5 back-and-forth movements per second.

11. The method of claim 9 wherein the colloidal solution is supplied to the blood flow path by a tube, wherein the tube is interposed between two pressing plates, and wherein the pressing plates are moved back and forth by a motor.

12. The method of claim 9, wherein the colloidal solution is moved alternately back and forth by a pump coupled to the blood inlet port and the blood outlet port.

* * * * *